US007078406B2

(12) United States Patent
Carver, Jr. et al.

(10) Patent No.: US 7,078,406 B2
(45) Date of Patent: Jul. 18, 2006

(54) SUBSTITUTED DIPHENYLOXAZOLES, THE SYNTHESIS THEREOF, AND THE USE THEREOF AS FLUORESCENCE PROBES

(75) Inventors: Theodore E. Carver, Jr., Downingtown, PA (US); James M. Rinker, Reading, PA (US)

(73) Assignee: Johnson & Johnson Pharmaceutical Research & Development, L.L.C., Raritan, NJ (US)

( * ) Notice: Subject to any disclaimer, the term of this patent is extended or adjusted under 35 U.S.C. 154(b) by 0 days.

(21) Appl. No.: 10/891,259

(22) Filed: Jul. 14, 2004

(65) Prior Publication Data

US 2004/0248851 A1  Dec. 9, 2004

Related U.S. Application Data

(62) Division of application No. 10/267,118, filed on Oct. 9, 2002, now Pat. No. 6,815,445.

(60) Provisional application No. 60/327,307, filed on Oct. 9, 2001.

(51) Int. Cl.
*A61K 31/497* (2006.01)
(52) U.S. Cl. ................ 514/254.02; 514/365; 514/374; 424/9.6
(58) Field of Classification Search ............ 514/254.02, 514/365, 374; 424/9.6
See application file for complete search history.

(56) References Cited

U.S. PATENT DOCUMENTS

| | | | |
|---|---|---|---|
| 5,260,207 A | 11/1993 | Pantoliano et al. | |
| 5,355,215 A | 10/1994 | Schroeder et al. | |
| 5,463,071 A | 10/1995 | Himmelsbach et al. | |
| 5,463,564 A | 10/1995 | Agrafiotis et al. | |
| 5,962,685 A | 10/1999 | Ueda et al. | |
| 6,020,141 A | 2/2000 | Pantoliano et al. | |
| 6,037,130 A | 3/2000 | Tyagi et al. | |
| 6,197,258 B1 | 3/2001 | Thompson et al. | |
| 6,291,191 B1 | 9/2001 | Pantoliano et al. | |
| 6,602,702 B1 | 8/2003 | McDevitt et al. | |

FOREIGN PATENT DOCUMENTS

| | | |
|---|---|---|
| WO | WO 95/13067 A1 | 5/1995 |
| WO | WO 97/14679 A2 | 4/1997 |
| WO | WO 97/29774 A1 | 8/1997 |
| WO | WO 97/42500 A1 | 11/1997 |
| WO | WO 99.04780 A1 | 2/1999 |
| WO | WO 01/06239 A2 | 1/2001 |
| WO | WO 2001006253 | 1/2001 |
| WO | WO 01/71317 A1 | 9/2001 |

OTHER PUBLICATIONS

Diwu et al., 1997, Photochemistry and Photobiology, 66(4), pp. 424-431.*

McDevitt et al., "Detection system based on an . . . ", CAS:134:128190 (2001).
Bagshaw, C.R. and Harris, D.A., "Measurement of Ligand Binding to Proteins," in Spectrophotometry & Spectrofluorimetry, Bashford, C.L., and Harris, D.A., eds., IRL Press, Oxford, England, (1987) pp. 91-113.
Barcelo, F., et al., "A Scanning calorimetric study of natural DNA and antitomoral anythracycline antibiotic-DNA complexes." Chem.-Biol. Interactions (1990) 74: 315-324, Elsevier Scientific Publishers Ireland, Ltd.
Bell, J. E., "Fluorescence: Solution Studies," in Spectroscopy in Biochemistry, vol. I, Bell, J. E., ed., CRC Press, Inc. Boca Raton, FL, (1981) pp. 155-194.
Bergeron, R.J., and McManis, J.S., "Total Synthesis of (±)-15-Deoxyspergualin," J. Org. Chem. (1992) 52:2497-2502, American Chemical Society.
Bernatowicz, M.S., et al., "1 H-pyrazole-1-carboxamidine Hydrochloride: An Attractive Reagent for Guanylation of Amines and Its Application to Peptide Synthesis", J. Org. Chem. (1992) 57:2497-2502, American Chemical Society.
Bernatowicz, M.S., et al., "Urethane Protected Derivitives of 1-Guanykpyrazole for the Mild and Efficient Preparation of Guanidines," Tetrahedron Lett. (1993) 34:3389-3392, Pergamon Press, Ltd.
Brand, L., and Gohlke, J.R., "Fluorescence probes for structure," Annu. Rev. Biochem. (1972) 41:843-868, Annual Reviews, Inc.
Brandts, J.F., and Lin, L-N., Study of Strong to Ultralight Protein Interactions Using Differential Scanning Calorimetry, Biochemistry (1990) 29:6927-6940, American Chemical Society.
Callis, P. R., et al., "The Theory of Two-Photon-Induced Fluorescence Anistrophy," in Topics in Fluorescence Spectroscopy, vol. 5, Lakowicz, J. R., ed., Plenum Press, New York, NY (1997) pp. 1-42.

(Continued)

*Primary Examiner*—Taofiq Solola
*Assistant Examiner*—Robert Shiao
(74) *Attorney, Agent, or Firm*—Wilson Sonsini Goodrich & Rosati

(57) ABSTRACT

The present invention is directed to a compound of Formula I:

(I)

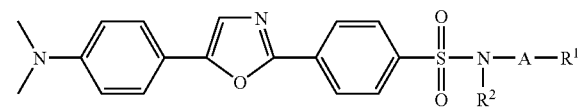

wherein A, $R^1$, and $R^2$ are defined herein. The present invention is also directed to compositions comprising compounds of Formula I, methods of using compounds of Formula I, and methods of making compounds of Formula I.

7 Claims, No Drawings

OTHER PUBLICATIONS

Clegg, R. M., et al., "Fluorescence Resonance Energy Transfer Analysis of the Structure of the Four-Way DNA Junction," Biochemistry (1992) 31: 4846-4856, American Chemical Society.

Clegg, R. M., et al., "Observing the helical geometry of double-stranded DNA in solution by flurescence resonance energy transfer," Proc. Natl. Acad. Sci. USA (1993) 90:2994-2998, National Academy Press.

Davidson, A.R. et al., "Cooperatively folded proteins in random sequence libraries," Nat. Struct. Biol. (1995) 2:856-864, Nature Publishing Company.

Denk, W., et al., "Two-photon Laser Scanning Fluorescence Microscopy," Science (1990) 248: 73-76, American Association for the Advancement of Science.

Diwu, Z., et al., "Fluorescent Molecular Probes II. The Synthesis, Spectral Properties and Use of Fluorescent Solvatochromic Dapoxyl™ Dyes," Photochem. Photobiol. (1997) 66: 424-431, Allen Press.

Diwu, A., et al., "The Spectral Properties and Biological Applications of Solvatochromic Dapoxl™ Dyes," in Advances in Fluorescence Sensing Technology IV, Lakowicz, J. R., et al., eds., S P I E-International Society for Optical Engineering, Bellingham, Washington, (1999), pp. 256-264.

Diwu, Z., et al. "Fluorescent molecular probes VI. The spectral properties and potential biological applications of water-soluble Dapoxyl™ sulfonic acid," Journal of Photochemistry and Photobuilogy A: Chemistry (Feb. 2000) 131:95-100, Elsevier Science S. A.

Eftink, M.R., "The Use of Flurscence Methods to Monitor Unfolding Tranisitions in Proteins," Biophys. J. (1994) 66:482-501, The Biophysical Society.

Epps, D.E., et al., "The Ligand Affinity of Proteins Measured by Isothermal Denaturation Kinetics," Anal. Biochem. (May 2001) 292:40-50, Academic Press.

Fedyunyaeva, I. A., and Shershukov, B.M., "4-(5-Aryl-2-oxazolyl) benzenesulfonic acid derivitives containing a dimethylamino group," Khim. Geterotsikl. Soedin. (1993) 2:234-237.

Fersht, A., "Nucleation mechanisms in protein folding," Curr. Opin. Struct. Biol. (1993) 7:3-9, Current Biology, Ltd.

Lee, M., et al., "In Vitro Cytoxicity of GC Sequence Directed Alkylating Agents Related to Distamycin," J. Med. Chem. (1993) 36:863-870, American Chemical Society.

Maier, G.V. et al., "Spectral-luminescent properties of sulfonyl-substituted oxazole," Zh. Prikl. Spektrosk. (1991) 55: 576-581.

Martson, F.A.O., "The purification of eukaryotic polypeptide synthesized in *Escherichia coli*," Biochem, J. (1986) 240:1-12, The Biochemical Society.

Miller, A.E., and Bischoff, J.J. "A Facile Conversion of Amino Acids to Guanidino Acids," Synthesis (1986) 9:777-779, Georg Thiem Verlag Stuttgart.

Ozaki, H., and McLaughlin, L.W., "The estimation of distances between specific backbone-labeled sites in DNA using fluorescence resonance energy transfer," Nucl, Acids Res. (1992) 20:5205-5214, Oxford University Press.

Rockwell, P. L., and Storey, B.T., "Kinetics of Onset of Mouse Sperm Acrosome Reaction Induced by Solubolized Zona Pellucida: Fluorimetric Determination of Loss of pH Gradient Between Acrosomal Lumen and Medium Monitored by Dapoxl (2-Aminoethyl) Sulfonamide and of Intracellular $Ca^{2+}$ Changes Monitored by Fluo-3," Mol. Reprod. Dev. (Mar. 2000) 55:335-349, Wiley-Liss, Inc.

Schellman, J.A., Communications to the editor. The effect of Binding on the Melting Temperature of Biopolymers (1976) 15: 999-1000, John Wiley & Sons, Inc.

Schellman, J.A., "The relation between the free energy of interaction and binding," Biophys. Chem. (1993) 45:273-279, Elsevier Science Publishers B.V.

Schellman, J.A., "Macromolecular Binding," Biopolymers (1975) 14:999-1018, John Wiley & Sons, Inc.

Shimada, K., and Mitamura, K., "Derivatization of thiol-containing compounds," J. Chromatogr. B. Biomed. Appl. (1994) 659:227-241, Elsevier.

Skepper, J.N., et al., "How are $Ca^{2+}$ signals regulated by microtubules?" J. Physiol. (Sep. 2000) 527:72P, The Physiological Society.

Thompson, R.B., et al., "Improved fluorophores for zinc biosensing using carbonic anhydrase," in Systems and Technologies for Clinical Diagnostics and Drug Discovery II, vol. 3603, Cohn, G.E., et al, eds., S P I E-International Society for Optical Engineering, (1999) pp. 14-22, Bellingham, Washington.

Thompson, R.B., et al., "Zinc biosensing with multiphoton excitation using carbonic anhydrase and improved flurophores," J. Biomed. Opt. (Jan. 2000) 5:17-22, S P I E-International Society for Optical Engineering.

Volkov, V.M., et al., "Lasting in solutions of some diaryl-substituted oxazoles," Zh. Prikl. Spektrosk (1979) 31: 635-638.

Weber, P.C., et al., "Structure-Based Design of Synthetic Azobenzene Ligands for Streptavidin," J. Am. Chem. Soc. (1994) 116:2717-2724, American Chemical Society.

Wiseman, T., et al., "Rapid Measurement of Binding Constants and Heats of Binding Using a New Titration Calorimeter," Anal. Biochem. (1989) 179:131-137, Academic Press, Inc.

Yan, B., et al., "Determination of the Absolute Amount of Resin-Bound Hydroxyl or Carbonyl Groups for the Optimization of Solid-Phase Combinatorial and Parallel Organic Synthesis," Anal. Chem, (1999) 71:4564-4571, American Chemical Society.

Capulus Database, Assession No. 1994:54476, Caplus English language abstract for Fedyunyaeva, I.A., and Shershukov, B.M., "4-(5-Aryl2-oxazolyl) benzenesulfonic acid derivitives containing a dimethylamino group," Khim. Geterosikl. Soedin. (1993) 2:234-237 (Document AR7).

Caplus Database, Assession No. 1992 :30367, Caplus English abstract for Maier, J.V., et al. "Spectral-luminescent properties of sulfonyl-substituted oxazole," Zh. Prikl. Spektrosk (1991) 55:576-581 (Document AR8).

Caplus Databast, Assession No. 1980 :31622, Caplus English abstract fpr Volkov, V.M., et al. "Lasing in solutions of some diaryl-substituted oxazoles," Zh. Prikl. Spektrosk. (1979) 31:635-638 (Document AR12).

Molecular Probes, Inc., "Handbook of Fluorescent Probes and Research Chemicals," Catalog No. D-10460, Molecualr Probes, Inc. (1999).

Molecular Probes, Inc., "Handbook of Fluorescent Probes and Research Chemicals," Catalog No. D-10160, Molecular Probes, Inc. (1999).

Molecular Probes, Inc., "Handbook of Fluorescent Probes and Research Chemicals," Catalog No. D-10161, Molecular Probes, Inc. (1999).

Molecular Probes, Inc., "Handbook of Fluorescent Probes and Research Chemicals," Catalog No. D-10162, Molecular Probes, Inc. (1999).

Molecular Probes, Inc., "Handbook of Fluorescent Probes and Research Chemicals," Catalog No. D-10300, Molecular Probes, Inc. (1999).

Molecular Probes, Inc., "Handbook of Fluorescent Probes and Research Chemicals," Catalog No. D-10301, Molecular Probes, Inc. (1999).

Molecular Probes, Inc., "Handbook of Fluorescent Probes and Research Chemicals," Catalog No. D-10402, Molecular Probes, Inc. (1999).

Molecular Probes, Inc., "Handbook of Fluorescent Probes and Research Chemicals," Catalog No. D-10430, Molecular Probes, Inc. (1999).

Molecular Probes, Inc., "Handbook of Fluorescent Probes and Research Chemicals," Catalog No. D-12800, Molecular Probes, Inc. (1999).

Molecular Probes, Inc., "Handbook of Fluorescent Probes and Research Chemicals," Catalog No. D-12801, Molecular Probes, Inc. (1999).

* cited by examiner

U.S. 7,078,406 B2

SUBSTITUTED DIPHENYLOXAZOLES, THE SYNTHESIS THEREOF, AND THE USE THEREOF AS FLUORESCENCE PROBES

This application is a divisional of U.S. application Ser. No. 10/267,118, filed Oct. 9, 2002 now U.S. Pat. No. 6,815,445, which claims benefit under 35 U.S.C. § 119(e) of U.S. Provisional Application No. 60/327,307, filed Oct. 9, 2001, the contents of which are fully incorporated by reference herewith.

BACKGROUND OF THE INVENTION

1. Field of the Invention

The present invention relates to the area of diphenyloxazole derivates, the synthesis thereof, and the use thereof as fluorescence dyes and probes. The dyes of the present invention are derivatives of 2-(4'-sulfamoylphenyl)-5-(4''-dimethylaminophenyl)oxazoles.

2. Related Art

Fluorescence is the result of a three-stage process that occurs when certain molecules absorb energy. The three stages comprise: 1) excitation; 2) excited-state lifetime; and 3) fluorescence emission. During stage 1, excitation, a photon of a certain energy is absorbed by the fluorophore. The fluorophore is initially in its ground state ($S_0$). Absorption of the photon causes that fluorophore to become excited. The energy of the absorbed photon is transferred to an electron. The electron is transferred to a higher energy state. The fluorophore exists in an excited electronic singlet state ($S_{1'}$), also called an excited state. The excited state of the fluorophore exists for a finite time, typically $10^{-8}$ to $10^{-9}$ seconds. During the excited state, the fluorophore changes in its translational, vibrational, and electronic energy states, and is subject to interactions with its molecular environment. The excited fluorophore releases energy and returns to the ground state, $S_0$, by fluorescence emission. Other processes such as fluorescence energy transfer, intersystem crossing, and collisional quenching may also depopulate $S_1$. The ratio of the number of fluorescence photons emitted, during the emission stage, to the number of photons absorbed, during the excitation stage, is termed the quantum yield. The quantum yield is a measure of the efficiency of fluorescence in competition with other processes such as fluorescence energy transfer, intersystem crossing, and collisional quenching.

During the third stage, fluorescence emission, a photon of energy hv (where h is Planck's constant and v is the frequency of the photon) is emitted, returning the fluorophore to its ground state $S_0$. The energy of the emitted photon is lower than the energy of the photon absorbed during the excitation stage. The difference in energy can be attributed to dissipation through processes during the excited-state lifetime, such processes include fluorescence energy transfer, intersystem crossing, and collisional quenching. The difference in energy of the absorbed photon and the emitted photon is called the Stokes shift. The Stokes shift is fundamental to the sensitivity of fluorescence techniques because it allows emission photons to be detected against a low background, and at a different wavelength than the excitation photons.

Compounds that have fluorescent properties have numerous uses. Fluorescent molecules can be used in single molecule spectroscopy. Fluorescent molecules whose spectra or quantum yields are sensitive to their environments are valuable in the study of heterogeneous media, organized media, and biological media and many fluorescent dyes have been developed for these applications. However, many dyes either have short absorption and emission wavelengths (potentially causing high background due to the auto fluorescence of samples), low extinction coefficients, low quantum yields, or small Stokes shifts.

Fluorescent molecules are also useful in microplate thermal shift assays, as described in U.S. Pat. No. 6,020,141, which is fully incorporated by reference herein.

Rapid, high-throughput screening using fluorescence methodologies would also be facilitated by the use of fluorescence probe molecules that fluoresce at wavelengths longer than fluorescence molecules such as 1-anilinonaphthalene-8-sulfonate. That is because many molecules in compound and combinatorial libraries fluoresce at the same wavelengths at which presently available fluorescence probe molecules fluoresce. In addition, plastic microplates used in high-throughput screening assays may also fluoresce at the same wavelengths at which fluorescence probe molecules fluoresce.

Thus, there is a need for molecules that fluoresce when excited and provide emission spectra more useful than the spectra of 1-anilinonaph-thalene-8-sulfonate and derivatives thereof.

One class of fluorescent molecules is a group of compounds termed DAPOXYL dyes. DAPOXYL dyes contain the 4-(4'-(dimethylamino)phenyl)-2-(4'-sulfonylphenyl)oxazole moiety. A number of DAPOXYL dyes are known, including Dapoxyl® sulfonyl chloride; Dapoxy® carboxylic acid, succinimidyl ester; Dapoxyl® 3-sulfonamidopropionic acid, succinimidyl ester; Dapoxyl® (2-bromoacetamidoethyl)sulfonamide; Dapoxyl® 2-(3-(2-pyridyldithio)-propionamidoethyl) sulfonamide; Dapoxyl®) 3-sulfonamidophenylboronic acid; Dapoxyl® sulfonyl hydrazine; Dapoxyl® (2-aminoethyl)sulfonamide; Dapoxyl® sulfonic acid, sodium salt; and Dapoxyl® butylsulfonamide.

However, new derivatives of 2-(4'-sulfamoylphenyl)-5-(4'-dimethylaminophenyl)oxazole derivatives are needed that have improved solubility in both organic and aqueous media. New derivatives that are either more polar or less polar than existing oxazole dyes are needed. New oxazole derivatives that have improved utility in thermal shift assays are also needed.

SUMMARY OF THE INVENTION

A novel class of compounds that are useful as fluorescent molecules has been discovered. Fluorescent molecules, also called fluorophores, are known to be particularly suitable for biological applications in which a highly sensitive detection reagent is desirable. Fluorescent dyes are used to impart both visible color and fluorescence to other materials. The dyes of this invention are derivatives of 2-(4'-sulfamoylphenyl)-5-(4'-dimethylaminophenyl)oxazoles.

A first aspect of the present invention is directed to compounds of Formula I.

A second aspect of the present invention is directed to compositions comprising compounds of Formula I.

A third aspect of the present invention is directed to methods of making compounds of Formula I.

A fourth aspect of the present invention provides for a use of compounds of Formula I in a method for ranking the affinity of each of a multiplicity of different molecules for a target molecule which is capable of unfolding due to a thermal change.

A fifth aspect of the present invention provides for a use of the compounds of Formula I in a multi-variable method for ranking the affinity of a combination of two or more of a multiplicity of different molecules for a target molecule which is capable of unfolding due to a thermal change.

A sixth aspect of the present invention provides for a use of compounds of Formula I in a method for assaying a collection of a multiplicity of different molecules for a molecule which binds to a target molecule which is capable of unfolding due to a thermal change.

A seventh aspect of the present invention provides for a use of compounds of Formula I in a multi-variable method for ranking the efficacy of one or more of a multiplicity of different biochemical conditions for stabilizing a target molecule which is capable of unfolding due to a thermal change.

A eighth aspect of the present invention provides for a use of compounds of Formula I in a multi-variable method for optimizing the shelf life of a target molecule which is capable of unfolding due to a thermal change.

A ninth aspect of the present invention provides for a use of compounds of Formula I in a multi-variable method for ranking the efficacies of one or more of a multiplicity of different biochemical conditions to facilitate the refolding or renaturation of a sample of a denatured or unfolded protein.

An tenth aspect of the present invention provides for a use of compounds of Formula I in a multi-variable method for ranking the efficacy of one or more of a multiplicity of different biochemical conditions for facilitating the crystallization of a protein which is capable of unfolding due to a thermal change.

Further features and advantages of the present invention are described in detail below with reference to the accompanying drawings.

BRIEF DESCRIPTION OF THE DRAWINGS

The present invention is described with reference to the accompanying figures.

FIG. 1A provides the fluorescence emission spectra of 4-[5-(4-dimethylaminophenyl)oxazol-2-yl]-N-(2-guanidinoethyl)-benzenesulfonamide in methanol and in dimethylsulfoxide. Also provided is the fluoescence emission spectrum of the buffer. FIG. 1B provides part of the spectrum of FIG. 1A, showing the range from 0 to 10,000 cps.

FIG. 2 provides the fluorescence emission spectra of 4-[5-(4-dimethylaminophenyl)oxazol-2-yl]-N-(2-guanidinoethyl)-benzenesulfonamide (10 µM) mixed with thrombin (0.1 mg/mL) in buffer (50 mM HEPES, pH 7.5, 150 mM NaCl). The emission spectrum indicated by the squares was acquired with native (folded) thrombin, immediately after preparing the solution. The emission spectrum indicated by the triangles was obtained after heating the solution to 80° C. for five minutes to unfold the thrombin protein. The spectrum obtained after heating shows the increase in fluorescence emission and the red-shifted emission maximum.

FIG. 3 provides the individual fluorescent curves for three dyes 4-[5-(4-dimethylaminophenyl)oxazol-2-yl]-N-(2-guanidinoethyl)-benzene-sulfonamide, 5-(4″-dimethylaminophenyl)-2-(4′-phenyl)oxazole sulfonate, and 1,8-anilinonapthylene sulfonate) when analyzed in a Thermofluor® instrument using the protein PPAR-gamma as described in Example 3.

DETAILED DESCRIPTION OF THE INVENTION

A first aspect of the present invention is directed to a compound of Formula I:

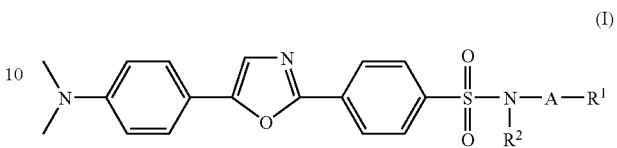

(I)

wherein
A is a single bond, alkylene, alkenylene, or alkynylene, wherein any of alkylene, alkenylene, and alkynylene is optionally substituted;
$R^1$ is cycloalkyl, cycloalkenyl, cycloheteroalkyl, cycloheteroalkenyl, aryl, heteroaryl, —$OR^3$, —$NR^3R^4$, —$SR^3$, —$S(O)R^3$, —$S(O)_2R^3$, —$C(O)H$, —$C(O)OR^3$, —$OC(O)R^3$, —$C(O)NR^3R^4$—$NR^3C(O)R^4$, —$OC(O)OR^3$, —$OC(O)NR^3R^4$, —$NR^3C(O)OR^4$, —$OS(O)_2OR^3$, —$S(O)_2OR^3$, —$S(O)OR^3$, —$OP(O)(OR^3)OR^4$, —$P(O)(OR^3)OR^4$, —$P(O)HOR^3$, amidino, guanidino, biguanidino, oxyguanidino, alkyliminoamino, formyliminoamino, or a chelator; and
$R^2$ is H, alkyl, alkenyl, alkynyl, aryl, arylalkyl, or cycloalkyl, wherein any of alkyl, alkenyl, alkynyl, aryl, arylalkyl, and cycloalkyl is optionally substituted; and
$R^3$ and $R^4$ are independently H, alkyl, alkenyl, alkynyl, aryl, heteroaryl, arylalkyl, or heteroarylalkyl, wherein any of alkyl, alkenyl, alkynyl, aryl, heteroaryl, arylalkyl, and heteroarylalkyl is optionally substituted;
and wherein
A is a single bond;
$R^1$, $R^2$, and A, together with N to which $R^1$, $R^2$, and A are attached, form a nitrogen-containing cycloheteroalkyl or cycloheteroalkenyl group, either of which is optionally substituted; and chemically acceptable salts thereof;
with the provisos that, when A is $C_{1-8}$ unsubstituted alkyl and $R^2$ is H or methyl, then $R^1$ is not —$NH_2$, —$NHCH_3$, —$N(CH_3)_2$, or —$NHC(O)CH_2Br$;
when A is $C_{1-3}$ unsubstituted alkyl and $R^2$ is H, then $R^1$ is not —$C(O)OH$, —$C(O)OCH_3$, or —$C(O)OCH_2CH_3$;
when A is $C_{1-3}$ unsubstituted alkyl and $R^2$ is H, then $R^1$ is not —$NHC(O)C_6F_5$;
when A is a single bond and $R^2$ is H or $CH_3$, then $R^1$ is not phenyl substituted with —$B(OH)_2$; and
when A is a single bond, $R^1$, $R^2$, and A, together with N to which $R^1$, $R^2$, and A are attached, do not form unsubstituted morpholinyl.

One subclass of compounds is a group of compounds of Formula I, wherein A is a single bond; and
$R^1$, $R^2$, and A, together with N to which $R^1$, $R^2$, and A are attached, form a nitrogen-containing cycloheteroalkyl or a nitrogen-containing cycloheteroalkenyl group, either of which is optionally substituted.

Within this first subclass of compounds, a preferred group of compounds is a group of compounds wherein $R^1$, $R^2$, and A, together with N to which $R^1$, $R^2$, and A are attached, form a nitrogen containing cycloheteroalkyl group. Suitable cycloheteroalkyl groups include 1-aziridinyl, 1-azetidinyl, 1-pyrrolidinyl, 1-piperidyl, 1-perhydroazepinyl, 1-perhydroazocinyl, 1-perhydroazoninyl, 1-perhydroazecinyl, perhydroquinolinyl, perhydroisoquinolinyl, 1-imidazolidinyl, 1-pirazolidinyl, 2-pirazolidinyl, 3-oxazolidinyl, 2-isoxazolidinyl, 3-thiazolidinyl, 2-isothiazoladinyl, 1-piperazinyl, 1-hexahydropyridazinyl, 1-hexahydropyrimidinyl, substituted morpholinyl, 2-(1,2-hexahydrothiazinyl), 3-(1,3-hexahydrothiazinyl), 4-(1,4-hexahydrothiazinyl), 2-(1,2,5-oxadiazolidinyl), 2-(1,2,5-thiadiazolidinyl), and oxathiazolidinyl.

Another preferred group of compounds within this first subclass of compounds is a group of compounds wherein $R^1$, $R^2$, and A, together with N to which $R^1$, $R^2$, and A are attached, form a 5–6 membered nitrogen-containing cycloheteroalkyl group containing 1 or 2 heteroatoms, wherein said cycloheteroalkyl group is optionally substituted. Suitable substituted, nitrogen-containing cycloheteroalkyl groups include the cycloheteroalkyl groups listed above containing one or more substitutents selected from the group consisting of $C_{1-6}$ alkyl, hydroxy, oxo, nitro, halogen, $C_{1-6}$ alkoxy, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, $C_{2-6}$ hydroxyalkoxy, ($C_{1-6}$)alkoxy($C_{2-6}$)alkoxy, mono- and di- $C_{1-4}$ alkylamino ($C_{2-6}$)alkoxy, $C_{2-10}$ mono(carboxyalkyl) amino, bis($C_{2-10}$ carboxyalkyl) amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ ar($C_{1-6}$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, and perfluoroethoxy.

Preferably, said one or more substitutents on said substituted, nitrogen-containing cycloheteroalkyl group are independently selected from the group consisting of $C_{1-6}$ alkyl, hydroxy, oxo, nitro, halogen, $C_{1-6}$ alkoxy, amino, mono ($C_{1-4}$)alkylamino, di($C_{1-4}$)alkylamino, guanidine, and carboxy.

Another preferred group of compounds within this first subclass of compounds is a group of compounds wherein $R^1$, $R^2$, and A, together with N to which $R^1$, $R^2$, and A are attached, form a nitrogen-containing cycloheteroalkenyl group, wherein said cycloheteroalkenyl group is optionally substituted. Suitable nitrogen-containing cycloheteroalkenyl groups include 2-pyrroline-1-yl, 3-pyrroline-1-yl, 2-imidazolin-1-yl, 3-imidazolin-1-yl, 4-imidazolin-1-yl, 3-pirazoline-2-yl, and 3-pirazoline-1-yl. Suitable substituted, nitrogen-containing cycloheteroalkenyl groups include the cycloheteroalkyl groups listed above containing one or more substitutents selected from the group consisting of $C_{1-6}$ alkyl, hydroxy, oxo, nitro, halogen, $C_{1-6}$ alkoxy, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, $C_{2-6}$ hydroxyalkoxy, ($C_{1-6}$)alkoxy($C_{2-6}$)alkoxy, mono- and di- $C_{1-4}$ alkylamino ($C_{2-6}$)alkoxy, $C_{2-10}$ mono(carboxyalkyl)amino, bis($C_{2-10}$ carboxyalkyl) amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ar($C_{1-6}$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, and perfluoroethoxy.

Preferably, said one or more substituents on said substituted, nitrogen-containing cycloheteroalkenyl group are selected from the group consisting of $C_{1-6}$ alkyl, hydroxy, oxo, nitro, halogen, $C_{1-6}$ alkoxy, amino, mono($C_{1-4}$)alkylamino, di($C_{1-4}$)alkylamino, guanidine, and carboxy.

A second subclass of compounds is a group of compounds of Formula I wherein A is alkylene, alkenylene, or alkynylene, any of which is optionally substituted; and
$R^1$ is cycloalkyl, cycloalkenyl, cycloheteroalkyl, or cycloheteroalkenyl, any of which is optionally substituted.

A preferred group of compounds within said second subclass of compounds is a group of compounds wherein A is $C_{1-8}$ alkylene, $C_{1-8}$ alkenylene, or $C_{1-8}$ alkynylene, any of which is optionally substituted, more preferably $C_{1-6}$ alkylene, $C_{1-6}$ alkenylene, or $C_{1-6}$ alkynylene, any of which is optionally substituted.

A preferred group of compounds within said second subclass of compounds is a group of compounds wherein $R^1$ is cycloalkyl or cycloalkenyl, either of which is optionally substituted. Preferably, $R^1$ is a 4–8 membered, more preferably a 5–7 membered optionally substituted cycloalkyl or optionally substituted cycloalkenyl group. When $R^1$ is a substituted cycloalkyl or substituted cycloalkenyl group, the substituents on said substituted group are preferably 1 or 2 of $C_{1-6}$ alkyl, hydroxy, nitro, halogen, $C_{1-6}$ alkoxy, $C_{1-6}$ aminoalkoxy, amino, mono($C_{1-4}$)alkylamino, di($C_{1-4}$)alkylamino, $C_{2-6}$ alkoxycarbonyl, carboxy, $C_{2-6}$ hydroxyalkoxy, mono- and di- $C_{1-4}$ alkylamino ($C_{2-6}$)alkoxy, $C_{2-10}$ mono (carboxyalkyl)amino, bis($C_{2-10}$ carboxyalkyl) amino, amidino, guanidino, $C_{1-6}$ alkyliminoamino, formyliminoamino, cyano, trifluoromethoxy, or perfluoroethoxy.

Another preferred group of compounds within said second subclass of compounds is a group of compounds wherein $R^1$ is cycloheteroalkyl or cycloheteroalkenyl, either of which is optionally substituted. Preferably, $R^1$ is a 4–8 membered, more preferably a 5–7 membered optionally substituted cycloheteroalkyl or optionally substituted cycloheteroalkenyl group. When $R^1$ is a substituted cycloalkyl or substituted cycloalkenyl group, the substituents on said substituted group are preferably 1 or 2 of $C_{1-6}$ alkyl, hydroxy, nitro, halogen, $C_{1-6}$ alkoxy, $C_{1-6}$ aminoalkoxy, amino, mono($C_{1-4}$)alkylamino, di($C_{1-4}$)alkylamino, $C_{2-6}$ alkoxycarbonyl, carboxy, $C_{2-6}$ hydroxyalkoxy, mono- and di($C_{1-4}$)alkylamino ($C_{2-6}$)alkoxy, $C_{2-10}$ mono(carboxyalkyl) amino, bis($C_{2-10}$ carboxyalkyl) amino, amidino, guanidino, $C_{1-6}$ alkyliminoamino, formyliminoamino, cyano, trifluoromethoxy, or perfluoroethoxy.

A third subclass of compounds is a group of compounds of Formula I wherein A is substituted alkylene, substituted alkenylene, or substituted alkynylene; and $R^1$ is —$OR^3$ or —$NR^3R^4$.

A preferred group of compounds within said third subclass of compounds are compounds according to Formula I wherein A is substituted alkylene, substituted alkenylene, or substituted alkynylene; and $R^1$ is —$OR^3$ or —$NR^3R^4$. Another preferred group of compounds within said third subclass of compounds are compounds according to Formula I wherein A is substituted alkylene, substituted alkenylene, or substituted alkynylene; and $R^1$ is —$OR^3$ or —$NR^3R^4$.

Another preferred group of compounds of the third subclass of compounds are compounds wherein A is substituted alkylene. Said substituted alkylene groups may be branched or straight chain alkylene groups. Said alkylene may be substituted with one or more of hydroxy, nitro, halogen, $C_{1-6}$ alkoxy, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, $C_{2-6}$ hydroxyalkoxy, ($C_{1-6}$)alkoxy($C_{2-6}$)alkoxy, mono- and di- $C_{1-4}$ alkylamino ($C_{2-6}$)alkoxy, $C_{2-10}$ mono(carboxyalkyl)

amino, bis($C_{2-10}$ carboxyalkyl) amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-1}$ ar($C_{1-6}$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, or perfluoroethoxy.

Preferably, said substituted alkylene is substituted with one or more of hydroxy, nitro, halogen, amino, mono($C_{1-4}$) alkylamino, di($C_{1-4}$)alkylamino, amidino, guanidino, $C_{1-6}$ alkyliminoamino, formyliminoamino, and carboxy.

Suitable values of A for said third subclass of compounds include 2-hydroxypropylene, 2-aminopropylene, 3-hydroxybutylene, 2-hydroxybutylene, 2-aminobutylene, 3-aminobutylene, 2,3-dihydroxybutylene, 1,2-dihydroxybutylene, 1,3-dihydroxybutylene, 1,2-diaminobutylene, 1,3-diaminobutylene, 2,3-diaminobutylene, 1-amino-2-hydroxybutylene, 2-amino-1-hydroxybutylene, 1-hydroxymethylethylene, 2-hydroxymethylethylene, 1,1-bis(hydroxymethyl)ethylene, 2,2-bis(hydroxymethyl)ethylene, 2,2-bis(aminomethyl)ethylene, 1,1-bis(aminomethyl)ethylene, and 1-hydroxymethyl-4-methylaminopent-2-enylene.

Another group of preferred compounds of said third subclass of compounds are compounds wherein $R^2$ is H or $C_{1-6}$ alkyl.

Other preferred compounds of said third subclass of compounds are compounds wherein said alkylene is substituted with two or more OH.

A fourth subclass of compounds is a group of compounds of Formula I wherein

A is alkylene, alkenylene, or alkynylene, any of which is optionally substituted; and $R^1$ is aryl or heteroaryl, either of which is optionally substituted.

A preferred group of compounds within said fourth subclass of compounds are compounds according to Formula I wherein A is $C_{1-8}$ alkylene, $C_{2-8}$ alkenylene, or $C_{2-8}$ alkynylene, any of which is optionally substituted. A preferred group of compounds within said fourth subclass of compounds are compounds according to Formula I wherein A is $C_{1-6}$ alkylene, $C_{2-6}$ alkenylene, or $C_{2-6}$ alkynylene, any of which is optionally substituted.

Preferably, A is $C_{3-8}$ alkylene, $C_{4-8}$ alkenylene, or $C_{4-8}$ alkynylene. Preferably, $R^1$ is substituted aryl or substituted heteroaryl. When $R^1$ is a substituted aryl or substituted heteroaryl group, the substituents on said substituted group are preferably 1 or 2 of $C_{1-6}$ alkyl, hydroxy, nitro, halogen, $C_{1-6}$ alkoxy, $C_{1-6}$ aminoalkoxy, amino, mono($C_{1-4}$)alkylamino, di($C_{1-4}$)alkylamino, $C_{2-6}$ alkoxycarbonyl, carboxy, $C_{2-6}$ hydroxyalkoxy, mono- and di- $C_{1-4}$ alkylamino ($C_{2-6}$)alkoxy, $C_{2-10}$ mono(carboxyalkyl)amino, bis($C_{2-10}$ carboxyalkyl) amino, amidino, guanidino, $C_{1-6}$ alkyliminoamino, formyliminoamino, cyano, trifluoromethoxy, or perfluoroethoxy.

A fifth subclass of compounds is a group of compounds of Formula I wherein A is a single bond; and $R^1$ is cycloalkyl, cycloalkenyl, cycloheteroalkyl, cycloheteroalkenyl, any of which is optionally substituted.

A preferred group of compounds within said fifth subclass of compounds is a group of compounds wherein $R^1$ is cycloalkyl or cycloalkenyl, either of which is optionally substituted. Preferably, $R^1$ is a 4–8 membered, or preferably a 5–7 membered optionally substituted cycloalkyl or optionally substituted cycloalkenyl group. When $R^1$ is a substituted cycloalkyl or substituted cycloalkenyl group, the substituents on said substituted group are preferably 1 or 2 of $C_{1-6}$ alkyl, hydroxy, nitro, halogen, $C_{1-6}$ alkoxy, $C_{1-6}$ aminoalkoxy, amino, mono($C_{1-4}$)alkylamino, di($C_{1-4}$)alkylamino, $C_{2-6}$ alkoxycarbonyl, carboxy, $C_{2-6}$ hydroxyalkoxy, mono- and di-$C_{1-4}$ alkylamino ($C_{2-6}$)alkoxy, $C_{2-10}$ mono (carboxyalkyl)amino, bis($C_{2-10}$ carboxyalkyl) amino, amidino, guanidino, $C_{1-6}$ alkyliminoamino, formyliminoamino, cyano, trifluoromethoxy, or perfluoroethoxy.

Another preferred group of compounds within this fifth subclass of compounds is a group of compounds wherein $R^1$ is cycloheteroalkyl or cycloheteroalkenyl, wither of which is optionally substituted. Preferably, $R^1$ is a 4–8 membered, more preferably a 5–7 membered optionally substituted cycloheteroalkyl or optionally substituted cycloheteroalkenyl group. When $R^1$ is a substituted cycloalkyl or substituted cycloalkenyl group, the substituents on said substituted group are preferably 1 or 2 of $C_{1-6}$ alkyl, hydroxy, nitro, halogen, $C_{1-6}$ alkoxy, $C_{1-6}$ aminoalkoxy, amino, mono($C_{1-4}$) alkylamino, di($C_{1-4}$)alkylamino, $C_{2-6}$ alkoxycarbonyl, carboxy, $C_{2-6}$ hydroxyalkoxy, mono- and di-$C_{1-4}$ alkylamino ($C_{2-6}$)alkoxy, $C_{2-10}$ mono(carboxyalkyl)amino, bis($C_{2-10}$ carboxyalkyl) amino, amidino, guanidino, $C_{1-6}$ alkyliminoamino, formyliminoamino, cyano, trifluoromethoxy, or perfluoroethoxy.

Within this preferred group of compounds, it is noted that the nitrogen of the sulfamoyl group of Formula I may be bonded directly to a heteroatom of said cycloheteroalkyl or cycloheteroalkenyl, either of which is optionally substituted, when chemically feasible and stable. For example, if $R^1$ is an unsubstituted piperidine group, nitrogen of the sulfamoyl group of Formula I may be bonded directly to the nitrogen of the piperidine group.

A sixth subclass of compounds is a group of compounds of Formula I wherein A is alkylene, alkenylene, or alkynylene, any of which is optionally substituted; and $R^1$ is —C(O)O$R^3$, —C(O)NH$R^3$, —C(O)NHO$R^3$, —OC(O)NH$R^3$, —OC(O)O$R^3$, —OS(O)$_2$O$R^3$, —S(O)$_2$O$R^3$, —OP(O)(OH)O$R^3$, or —P(O)(OH)O$R^3$.

A preferred group of compounds within said sixth subclass of compounds are compounds according to Formula I wherein A is $C_{1-8}$ alkylene, $C_{2-8}$ alkenylene, or $C_{2-8}$ alkynylene, any of which is optionally substituted. A preferred group of compounds within said sixth subclass of compounds are compounds according to Formula I wherein A is $C_{1-6}$ alkylene, $C_{2-6}$ alkenylene, or $C_{2-6}$ alkynylene, any of which is optionally substituted.

Preferably, A is a substituted $C_{1-8}$ alkylene group substituted with one or more of hydroxy, nitro, halogen, $C_{1-6}$ alkoxy, $C_{1-6}$ aminoalkoxy, amino, mono($C_{1-4}$)alkylamino, di($C_{1-4}$)alkylamino, $C_{2-6}$ alkoxycarbonyl, carboxy, $C_{2-6}$ hydroxyalkoxy, mono- and di- $C_{1-4}$ alkylamino ($C_{2-6}$) alkoxy, $C_{2-10}$ mono(carboxyalkyl)amino, bis($C_{2-10}$ carboxyalkyl) amino, amidino, guanidino, $C_{1-6}$ alkyliminoamino, formyliminoamino, cyano, trifluoromethoxy, or perfluoroethoxy.

A seventh subclass of compounds is a group of compounds of Formula I wherein

A is alkylene, alkenylene, or alkynylene, any of which is optionally substituted; and $R^1$ is amidino, guanidino, biguanidino, oxyguanidino, alkyliminoamino, or formyliminoamino.

A preferred group of compounds within said seventh subclass of compounds are compounds according to Formula I wherein A is $C_{1-8}$ alkylene, $C_{2-8}$ alkenylene, or $C_{2-8}$ alkynylene, any of which is optionally substituted. A preferred group of compounds within said seventh subclass of compounds are compounds according to Formula I wherein A is $C_{1-6}$ alkylene, $C_{2-6}$ alkenylene, or $C_{2-6}$ alkynylene, any of which is optionally substituted.

An eigth subclass of compounds is a group of compounds of Formula I wherein $R^1$ is a chelator. When $R^1$ is a chelator, the chelator may also optionally include a linker group that connects A to the chelator. Preferred chelators are nitrolotriacetic acid, EDTA, bipyridyl, and histindinyl.

A ninth subclass of compounds is a group of compounds according to Formula I wherein $R^1$, $R^2$, and A, together with N to which said $R^1$, $R^2$, and A are attached, form a chemical moiety that is ionized at about pH 7. A preferred group of compounds within said nineth subclass of compounds is a group of compounds wherein $R^1$, $R^2$, and A, together with N to which said $R^1$, $R^2$, and A are attached, form a chemical moiety that has a net charge of from −1 to −3. A preferred group of compounds within said nineth subclass of compounds is a group of compounds wherein $R^1$, $R^2$, and A, together with N to which said $R^1$, $R^2$, and A are attached, form a chemical moiety that has a net charge of from −1 to −2. Another preferred group of compounds within said nineth subclass of compounds is a group of compounds wherein $R^1$, $R^2$, and A, together with N to which said $R^1$, $R^2$, and A are attached, form a chemical moiety that has a net charge of from +1 to +3. Another preferred group of compounds within said nineth subclass of compounds is a group of compounds wherein $R^1$, $R^2$, and A, together with N to which said $R^1$, $R^2$, and A are attached, form a chemical moiety that has a net charge of from +1 to +2. A preferred group of compounds within said nineth subclass of compounds is a group of compounds wherein $R^1$, $R^2$, and A, together with N to which said $R^1$, $R^2$, and A are attached, form a chemical moiety that has a net charge of 0.

Exemplary compounds of Formula I are
4-[5-(4-dimethylaminophenyl)oxazol-2-yl]-N-(2-pyrrolidin-1-yl-ethyl)benzenesulfonamide;
4-[5-(4-dimethylaminophenyl)oxazol-2-yl]-N-[3-(4-methylpiperazin-1-yl)propyl]benzenesulfonamide;
dimethyl-(4-{2-[4-(piperazine-1-sulfonyl)phenyl]oxazol-5-yl}-phenyl)amine;
dimethyl-(4-{2-[4-(4-methylpiperazine-1-sulfonyl)phenyl]oxazol-5-yl}phenyl)amine; 4-[5-(4-dimethylaminophenyl)oxazol-2-yl]-N-(4-methylpiperazin-1-yl)benzenesulfonamide;
2-{4-[5-(4-dimethylaminophenyl)oxazol-2-yl]-benzenesulfonylamino}succinic acid;
{4-[5-(4-dimethylaminophenyl)oxazol-2-yl]benzenesulfonylamino}-acetic acid;
({4-[5-(4-dimethylaminophenyl)oxazol-2-yl]benzenesulfonyl} methyl-amino)-acetic acid;
4-[5-(4-dimethylaminophenyl)oxazol-2-yl]-N-(2-guanidinoethyl)-benzenesulfonamide;
4-[5-(4-dimethylaminophenyl)oxazol-2-yl]-N-(2-hydroxy-1,1-bis-hydroxymethylethyl)benzenesulfonamide;
2-amino-5-{4-[5-(4-dimethylaminophenyl)oxazol-2-yl]-benzenesulfonylamino}pentanoic acid;
3-[4-[5-(4-dimethylaminophenyl)oxazol-2-yl]benzenesulfonyl]-thiazolidine-2,4-dicarboxylic acid dimethyl ester and salts thereof.

It is understood that the following compounds are excluded from the present invention: N-(2-aminoethyl)-4-[5-(4-dimethylaminophenyl)oxazol-2-yl]benzenesulfonamide; N-methyl-N-(2-(dimethylamino)ethyl)-4-[5-(4-dimethylaminophenyl)oxazol-2-yl]benzenesulfonamide; N-butyl-4-[5-(4-dimethylaminophenyl)oxazol-2-yl]benzenesulfonamide; 3-[4-[5-(4-dimethylaminophenyl)oxazol-2-yl]benzenesulfonamino]-phenylboronic acid; N-(2-(2-bromoacetamide)ethyl)-4-[5-(4-dimethylamino-phenyl)oxazol-2-yl]-benzenesulfonamide; N-(2-(3-(2-pyridyldithio)-propionamido)ethyl)-4-[5-(4-dimethylaminophenyl)oxazol-2-yl]benzene-sulfonamide; 3-[4-[5-(4-dimethylaminophenyl)oxazol2-yl]benzene-sulfonamino] propionic acid 2,5-dioxopyrrolidinyl ester; N-(2-(2-pentafluorobenzamido)ethyl)-4-[5-(4-dimethylaminophenyl)oxazol-2-yl]benzenesulfonamide; N-(2-aminoethyl)-4-[5-(4-dimethylaminophenyl)oxazol-2-yl]benzenesulfonamide; and dimethyl-[4-(2-[4-(morpholine-4-sulfonyl)phenyl]-oxazol-5-yl)phenyl]amine.

The present invention also includes a salt of a compound according to Formula I. The term salt refers to an acid- or base-addition salt of a compound according to Formula I. Acid-addition salts can be formed by adding an appropriate acid to the compound according to Formula I. Base-addition salts can be formed by adding an appropriate base to the compound according to Formula I, wherein said compound has an acid chemical group to react with said appropriate base. Said acid or base does not substantially degrade, decompose, or destroy said compound according to Formula I.

It is also understood that the present invention is considered to include stereoisomers as well as optical isomers, e.g., mixtures of enantiomers as well as individual enantiomers and diastereomers, which arise as a consequence of structural asymmetry in selected compounds of the present series.

The compounds of Formula I may also be solvated, especially hydrated. Hydration may occur during manufacturing of the compounds or compositions comprising the compounds, or the hydration may occur over time due to the hygroscopic nature of the compounds.

When any variable occurs more than one time in any constituent or in Formula I, its definition on each occurrence is independent of its definition at every other occurrence. Also, combinations of substituents and/or variables are permissible only if such combinations result in stable compounds.

Another aspect of the present invention is directed to compositions comprising a compound of Formula I and one or more chemically suitable solvents. Said chemically suitable solvent is selected from the group consisting of 1-butanol; 1-heptanol; 1-hexanol; 1-methoxy-2-propanol; 1-octanol; 1-pentanol; 1-propanol; 1,1,1-trichloro-methane; 1,1,2-trichloroethylene; 1,1,2-trichlorotrifluoroethane; 1,2-dichlorotetrafluoroethane; 1,3-butanediol; 1,3-butylene glycol methyl ether; 1,3-dimethoxy-2-propanol; 1,4-dioxane; 2-(2-n-butoxyethoxy)ethanol; 2-butanol; 2-butanone; 2-butoxyethanol acetate; 2-diethylaminoethanol; 2-ethoxyethanol acetate; 2-ethoxyethanol; 2-heptanone; 2-hexanone; 2-hydroxypropanoic acid; 2-methoxyethanol; 2-methylaminoethanol; 2-methylpropanol; 2-octanol; 2-pentanone; 2,4-toluenediisocyanate; 2,5-hexanedione; 3-(3-methylbutoxy)-1,2-propanediol; 3-butoxy-1,2-propane-diol; 3-ethoxy-1-propanol; 3-methoxy-1,2-propanediol; 3-methyl-2-butanone; 4-methyl-2-pentanol; 5-methyl-2-hexanone; 5-methyl-3-heptanone; α-terpineol; acetic acid; acetic acid, 2-methoxy-1-methylethyl ester; acetone; acrolein; amyl acetate; benzene; propyl acetate; butoxyethanol; butyl acetate; butylamine; methyl butyrate; butyl butyrate; carbon tetrachloride; catechol; chlorodifluoromethane; chloromethane; chloropentafluoroethane; chlorotrifluoromethane; cyclohexanol; cyclohexanone; d-limonene; diacetone alcohol; diamyl ether; dibutyl ether; dichlorodifluoromethane; dichlorofluoromethane; dichloromethane; diethanolamine; diethyl oxalate; diethylene glycol diethyl ether; diethylene glycol monoethyl ether acetate; diethylene glycol monomethyl ether; diethylene glycol monomethyl ether acetate; diethylene glycol; diethylene glycol dimethyl ether; diethylene glycol monoethyl ether; diisobutyl ketone; diisopropyl ether; diisopropylamine; dimethyl sulfoxide (DMSO); dimethylacetamide; dimethylamine; dimethylethanolamine; dipentene; diphenyl ether; dipropylene glycol monomethyl ether acetate; dipropylene glycol monomethyl ether; ethanol; ethyl acetate; ethyl propionate; ethylbenzene; ethylene glycol monophenyl ether; ethylene glycol; ethylene oxide; ethylene glycol methyl ether acetate; ethylene glycol dibutyl ether; ethylene glycol diethyl ether; ethylene glycol monobenzyl ether; formaldehyde; formic acid; furfural; furfuryl alcohol; γ-butyrolactone; heptane; hexamethyldisilazane; hexamethylene diisocyanate; hexane; hydroquinone; isooctyl alcohol; isopropyl alcohol; isopropylacetate; lactic acid, ethyl ester; lactic acid, methyl ester; lactic acid, butyl ester; lactic acid, amyl ester; m-xylene; methanesulfonic acid; methanol; methoxybenzene; methyl isobutyl ketone; methyl tert-butyl ether; methyl acetate; methyl isobutenyl ketone; methyl propionate; monoethanolamine; monoethylamine; monomethylamine; n-hexyl acetate; n-hexyl ether; N-methylpyrrolidone; N-nitrosodimethylamine; o-xylene; p-xylene; pentafluoropropyl alcohol; pentane; polyglycol E 200; propylene glycol monopropyl ether; propylene oxide; propylene carbonate; propyleneglycol diethyl ether; sec-butylacetate; sulfolane; terpinyl ethylene glycol ether; tetrachloroethylene; tetraethylene pentamine; tetraethylene glycol; tetrafluoromethane; tetrahydrofuran; tetrahydrofurfuryl alcohol; tetrahydropyran-2-methanol; toluene; trichlorofluoromethane; trichloromethane; triethanolamine; triethylamine; triethylene glycol; triethylene glycol dimethyl ether; trifluoromethane; trimethylene glycol; trioxane; VM & P Naphtha; water; xylene; or any combination thereof. Exemplary combinations include DMSO and water; methanol and water; ethanol and methanol; and isopropanol and water.

Definitions

The term "alkyl," as used herein, by itself or as part of another group, refers to both straight and branched chain radicals of up to 10 carbons, unless the chain length is limited thereto, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, and decyl.

The term "alkylene," as employed herein, by itself or as part of another group, refers to straight and branched chain radicals of up to 10 carbons, unless the chain length is limited thereto. Typical examples include methylene (—CH$_2$—), ethylene (—CH$_2$CH$_2$—), n-propylene (—CH$_2$CH$_2$CH$_2$—), isopropylene (—CH(CH$_3$)CH$_2$— and —CH$_2$CH(CH$_3$)—), n-butylene (—CH$_2$CH$_2$CH$_2$CH$_2$—), isobutylene, 3-methylpentylene (—CH$_2$CH$_2$CH(CH$_3$)CH$_2$CH$_2$—), hexylene, heptylene, octylene, nonylene, and decylene.

The term "alkenyl," as used herein, by itself or as part of another group, means a straight or branched chain radical of 2–10 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 8 carbon atoms in length, most preferably from 2 to 4 carbon atoms in length.

The term "alkenylene," as used herein, by itself or as part of another group, means a straight or branched chain radical of 2–10 carbon atoms, unless the chain length is limited thereto, said straight or branched chain radical containing at least one carbon—carbon double bond. Typical examples include ethenylene (—CH═CH—), propenylene (—CH═CHCH$_2$— and —CH$_2$CH═CH—), n-butenylene (—CH═CHCH$_2$CH$_2$—, —CH$_2$CH═CHCH$_2$—, —CH$_2$CH$_2$CH═CH—), and 3-methyl-2-pentenylene (—CH$_2$CH═C(CH$_3$)CH$_2$CH$_2$—), hexenylene, heptenylene, octenylene, nonenylene, and decenylene.

The term "alkynyl," as used herein, by itself or as part of another group, means a straight or branched chain radical of 2–10 carbon atoms, unless the chain length is limited thereto, wherein there is at least one triple bond between two of the carbon atoms in the chain, including, but not limited to, acetylenyl, 1-propynyl, 2-propynyl, and the like. Preferably, the alkynyl chain is 2 to 8 carbon atoms in length, most preferably from 2 to 4 carbon atoms in length.

The term "alkynylene," as used herein, by itself or as part of another group, means a straight or branched chain radical of 2–10 carbon atoms, unless the chain length is limited thereto, said straight or branched chain radical containing at least one carbon—carbon triple bond. Typical examples include ethynylene (—C≡C—), propynylene (—C≡CCH$_2$— and —CH$_2$C≡C—), n-butynylene (—C≡CCH$_2$CH$_2$—, —CH$_2$C≡CCH$_2$—, and —CH$_2$CH$_2$C≡C—), 4-methyl-2-pentynylene (—CH$_2$C≡CCH(CH$_3$)CH$_2$—), 1-butynylene, 2-butynylene, 3-butynylene, 4-butynylene, pentynylene, hexynylene, heptynylene, octynylene, nonynylene, and decynylene. In all instances herein where there is an alkenyl or alkynyl moiety as a substituent group, the unsaturated linkage, i.e., the vinylenyl or acetylenyl linkage, is preferably not directly attached to a nitrogen, oxygen, or sulfur moiety.

The term "alkoxy," as used herein, by itself or as part of another group, refers to any of the above alkyl groups linked to an oxygen atom. Typical examples are methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy.

The term "aryl," as employed herein, by itself or as part of another group, refers to monocyclic, bicyclic, or tricyclic aromatic groups containing from 6 to 14 carbons in the ring portion, preferably 6–10 carbons in the ring portion. Typical examples include phenyl, biphenyl, naphthyl, anthracenyl, and tetrahydronaphthyl.

The terms "aralkyl" and "arylalkyl," as employed herein, by itself or as part of another group, refer to alkyl groups as discussed above having an aryl substituent. Such groups include benzyl, phenylethyl, phenylpropyl, or 2-naphthylmethyl.

The term "heteroaryl," as employed herein, by itself or as part of another group, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αCH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

The term "heteroarylalkyl," as employed herein, by itself or as part of another group, refers to a heteroaryl group attached to an alkyl group. Typical examples include 2-(3- pyridyl)ethyl, 3-(2-furyl)-n-propyl, 3-(3-thienyl)-n-propyl, and 4-(1-isoquinolinyl)-n-butyl. The term "heteroaryl($C_{1-4}$)alkyl" as employed herein refers to a heteroalkyl group attached to a $C_{1-4}$ alkyl group.

The term "cycloalkyl," as employed herein, by itself or as part of another group, refers to cycloalkyl groups containing 3 to 10 carbon atoms. Typical examples are cyclopropyl, cyclobutyl, cyclopentyl, cyclohexyl, cycloheptyl, cyclooctyl, cyclononyl, and cyclodecyl. Cycloalkyl also includes bicyclic cycloalkyl groups. Typical bicyclic cycloalkyl groups include bicyclo[2.2.1]heptyl, bicyclo[3.1.1]heptyl, and bicyclo[2.2.2]octyl.

The term "cycloalkylalkyl," as employed herein, by itself or as part of another group, refers to a cycloalkyl group attached to an alkyl group. Typical examples are 2-cyclopentylethyl, cyclohexylmethyl, cyclopentylmethyl, 3-cyclohexyl-n-propyl, and 5-cyclobutyl-n-pentyl. The term "cycloalkyl($C_{1-4}$)alkyl" as employed herein, by itself or as part of another group, refers to a cycloalkyl group attached to a $C_{1-4}$ alkyl group.

The term "cycloalkenyl," as employed herein, by itself or as part of another group, refers to cycloalkenyl groups containing 3 to 10 carbon atoms and 1 to 3 carbon—carbon double bonds. Typical examples include cyclopropenyl, cyclobutenyl, cyclopentenyl, cyclohexenyl, cyclohexadienyl, cycloheptenyl, cycloheptadienyl, cyclooctenyl, cyclooctadienyl, cyclooctatrienyl, cyclononenyl, cyclononadienyl, and cyclodecenyl. Cycloalkenyl also includes bicyclic cycloalkenyl groups. Typical bicyclic cycloalkenyl groups include bicyclo[2.2.1]heptenyl, bicyclo[3.1.1]heptenyl, and bicyclo[2.2.2]octenyl.

The term "cycloalkenylalkyl," as employed herein, by itself or as part of another group, refers to a cycloalkenyl group attached to an alkyl group. Typical examples are 2-(2-cyclopentenyl)ethyl, 2-(2-cyclohexenyl)ethyl, 3-(2-cyclopentenyl)-n-propyl, and 4-(3-cyclohexenyl)-n-butyl. The term "cycloalkenylalkyl" as employed herein by itself or as part of another group refers to a cycloalkenyl group attached to a $C_{1-4}$ alkyl group.

The term "cycloheteroalkyl," as employed herein, by itself or as part of another group, refers to 5 to 14 ring atoms, containing carbon atoms and 1–4 heteroatoms. Typical examples include pyrrolidinyl, imidazolidinyl, pirazolidinyl, tetrahydrofuranyl, tetrahydropyranyl, piperidyl, piperazinyl, quinuclidinyl, morpholinyl, and dioxacyclohexyl. Cycloheteroalkyl also includes bicyclic cycloheteroalkyl groups. Typical bicyclic cycloheteroalkyl groups include quinuclidinyl, 7-azabicyclo[2.2.1]heptyl, 8-azabicyclo[3.2.1]octyl, and 4-thia-1-azabicyclo[3.2.0]heptane.

The term "cycloheteroalkylalkyl," as employed herein, by itself or as part of another group, refers to 5 to 14 ring atoms, containing carbon atoms and 1–4 heteroatoms, attached to an alkyl group. Typical examples include 2-(2-furanyl)ethyl, 3-(2-morpholinyl)-n-propyl, 4-(1-piperidyl)-n-butyl, and 2-(2-imidazolidinyl)ethyl. The term "cycloheteroalkyl($C_{1-4}$)alkyl" as employed herein, by itself or as part of another group, refers to 5 to 14 ring atoms, containing carbon atoms and 1, 2, 3, or 4 oxygen, nitrogen, or sulfur heteroatoms, attached to a $C_{1-4}$ alkyl group.

The term "cycloheteroalkenyl," as employed herein, by itself or as part of another group, refers to 5 to 14 ring atoms, containing carbon atoms, 1–4 heteroatoms, and 1–3 double bonds. Typical examples include pyrrolinyl, imidazolinyl, pirazolinyl, dihydropyridinyl, tetrahydropyridinyl, and dihydropyranyl. Cycloheteroalkenyl also includes bicyclic cycloheteroalkenyl groups. Typical bicyclic cycloheteroalkenyl groups include quinuclidinyl, 7-azabicyclo[2.2.1]heptenyl and 8-azabicyclo[3.2.1]octenyl.

The term "cycloheteroalkenylalkyl," as employed herein, by itself or as part of another group, refers to 5 to 14 ring atoms, containing carbon atoms, 1–4 heteroatoms, 1–3 double bonds, attached to an alkyl group. Typical examples include 2-(2-(1,2-dihydropyridinyl))ethyl and 3-(2-(1,2,3,6-tetrahydropyridinyl)-n-propyl. The term "cycloheteroalkenyl($C_{1-4}$)alkyl" as employed herein, by itself or as part of another group, refers to a cycloheteroalkenyl group attached to a $C_{1-4}$ alkyl group.

The term "alkylenedioxy," as employed herein, by itself or as part of another group, refers to a ring and is especially $C_{1-4}$ alkylenedioxy. Alkylenedioxy groups are optionally substituted with halogen (especially fluorine). Typical examples include methylenedioxy ($OCH_2O$) or difluoromethylenedioxy ($OCF_2O$).

The terms "halogen" or "halo," as employed herein, by itself or as part of another group, refers to chlorine, bromine, fluorine or iodine.

The terms "monoalkylamine" and "monoalkylamino," as employed herein, by itself or as part of another group, refers to the group $NH_2$ wherein one hydrogen has been replaced by an alkyl group, as defined above.

The terms "dialkylamine" and "dialkylamino," as employed herein, by itself or as part of another group, refers to the group $NH_2$ wherein both hydrogens have been replaced by alkyl groups, as defined above.

The term "hydroxyalkyl," as employed herein, by itself or as part of another group, refers to an alkyl group wherein one or more hydrogens thereof are substituted by one or more hydroxyl moieties.

The term "haloalkyl," as employed herein, by itself or as part of another group, refers to an alkyl group wherein one or more hydrogens thereof are substituted by one or more halo moieties. Typical examples include fluoromethyl, difluoromethyl, trifluoromethyl, trichloroethyl, trifluoroethyl, fluoropropyl, and bromobutyl.

The term "haloalkenyl," as employed herein, by itself or as part of another group, refers to an alkenyl group wherein one or more hydrogens thereof are substituted by one or more halo moieties.

The term "haloalkynyl," as employed herein, by itself or as part of another group, refers to an alkynyl group wherein one or more hydrogens thereof are substituted by one or more halo moieties.

The term "carboxyalkyl," as employed herein, by itself or as part of another group, refers to an alkyl group wherein one or more hydrogens thereof are substituted by one or more carboxylic acid moieties.

The term "heteroatom," as used herein, by itself or as part of another group, means an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

The abbreviation "t-Am," as used herein, by itself or as part of another group, refers to an active amyl moiety having the structure $CH_3CH_2(CH_3)_2C-$.

The term "nitrogen-containing," as used herein, by itself or as part of another group, refers to a chemical moiety that contains at least one nitrogen atom within said moiety. Specifically, nitrogen containing is used to modify moieties such as cycloheteroalkyl and cycloheteroalkenyl. For example, a nitrogen-containing cycloheteroalkyl group is a cycloheteroalkyl group, as defined above, wherein said group has at least one nitrogen atom as a part of the ring. Examples of nitrogen-containing cycloheteroalkyl groups include pyrrolidine, piperidine, morpholine, and 3-thiapyrrolidine. Examples of cycloheteroalkyl groups that are not included in the group of nitrogen-containing cycloheteroalkyl groups are tetrahydrofuran, tetrahydrothiophene, and thiapene.

The term "chelator," as used herein, by itself or as part of another group, refers to a chemical moiety that binds non-covalently to, or complexes with, one or more ions. Chelators can bind to lithium, calcium, sodium, magnesium, potassium, and/or other biologically important metal ions. The binding of the chelator to an ion can be determined by measuring the dissociation constant between a chelator and an ion. According to the invention, the dissociation constant $K_D$ between the chelator and the ion is from about $10^{-3}$ to about $10^{-15}$ $M^{-1}$. Preferably, the dissociation constant $K_D$ between the chelator and the ion is from about $10^{-6}$ to about $10^{-15}$ $M^{-1}$. When $R^1$ is a chelator, the chemical bond connecting $R^1$ to A may be on carbon atom of $R^1$ or a heteroatom of $R^1$. Preferably, the chemical bond connecting said chelator to A is on a carbon atom of said chelator.

Chelators include chemical moieties that bind to, or complex with, any cation or anion. Examples of chelators are well known in the art. Preferably, the chelator binds a metal cation. Suitable chelators are bipyridyl (bipy); terpyridyl (terpy); ethylenediaminetetraacetic acid (EDTA); crown ethers; aza-crown ethers; succinic acid; citric acid; salicylic acids; histidines; imidazoles; ethyleneglycol-bis-(beta-aminoethyl ether) N,N'-tetraacetic acid (EGTA); nitroloacetic acid; acetylacetonate (acac); sulfate; dithiocarbamates; carboxylates; alkyldiamines; ethylenediamine (en); diethylenetriamine (dien); nitrate; nitro; nitroso; $(C_6H_5)_2PCH_2CH_2P(C_6H_5)_2$ (diphos); glyme; diglyme; bis(acetylacetonate)ethylenediamine (acacen); 1,4,7,10-tetraazacyclododecanetetraacetic acid (DOTA), 1,4,7,10-tetraazacyclododecane-1,4,7-triacetic acid (DOTA), 1-oxa-4,7,10-triazacyclododecane-triacetic acid (OTTA), 1,4,7-triazacyclononanetriacetic acid (NOTA), 1,4,8,11-tetraazacyclotetradecanetetraacetic acid (TETA), DOTA-N-(2-aminoethyl) amide; DOTA-N-(2-aminophenethyl) amide; and 1,4,8,11-tetraazacyclotetradecane.

The term "ionized," as used herein, refers to a state of a compound or chemical moiety in which the positive and negative charges of said compound or chemical moiety are not balanced, or a state of a compound or chemical moiety in which there are positive and negative charges on adjacent or nonadjacent atoms and said compound or chemical moiety has no uncharged canonical representations. A compound or chemical moiety that is ionized has may have a net negative or positive charge. Preferably, the imbalance of positive and negative charge is due to either a gain or loss of one or more protons, respectively. The gain or loss of one or more protons may occur between functional groups within said compound or chemical moiety. A compound or chemical moiety that is zwitterionic is included within ionized compounds or chemical moieties, respectively. According to the present invention, a compound is ionized if at least about 89% of a sample of said compound or chemical moiety is ionized in an aqueous solution at pH 7, preferably at least about 98% of a sample of said compound or chemical moiety is ionized in an aqueous solution at pH 7.

A compound can be determined to be ionized by methods well known in the art, such as spectroscopically or potientiometrically. By way of example, a compound according to Formula I, wherein $R^1$, $R^2$, and A, together with N to which said $R^1$, $R^2$, and A are attached, form —N(CH$_3$)CH$_2$CH$_2$NHC(NH)NH$_2$. It is determined that, in an aqueous solution at about pH 7, at least 98% the molecules of said compound contain said —N(CH$_3$)CH$_2$CH$_2$NHC(NH)NH$_2$ in the protonated form. Thus, according to the present invention, a compound according to Formula I, wherein $R^1$, $R^2$, and A, together with N to which said $R^1$, $R^2$, and A are attached, form —N(CH$_3$)CH$_2$CH$_2$NHC(NH)NH$_2$ would be considered fall within said nineth subclass of compounds.

The term "substituted," as used herein, refers to a group or groups being substituted with one or more substituents independently selected from the group consisting of hydroxy, oxo, nitro, trifluoromethyl, halogen, $C_{1-6}$ alkoxy, $C_{6-10}$ ar($C_{1-6}$)alkoxy, $C_{1-6}$ alkylenedioxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, $C_{2-6}$ hydroxyalkoxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl)amino, bis($C_{2-10}$ carboxyalkyl)amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ar($C_{1-6}$)alkylsulfonyl, $C_{1-6}$ alkylsulfinyl, $C_{1-6}$ alkylsulfonamido, $C_{6-10}$ arylsulfonamido, $C_{6-10}$ar($C_{1-6}$) alkylsulfonamido, $C_{2-6}$ carboxyalkoxy, $C_{2-6}$ carboxyalkyl, carboxyalkylamino, cyano, trifluoromethoxy, perfluoroethoxy, guanidine, amidino, oxyguanidino, alkylimino, formylimino, acyl nitrile, acyl azide, acetyl azide, dichlorotriazene, isothiocyante, sulfonyl halide, sulfosuccinimidyl ester, isocyante, acyl halide, aldehyde, haloacetamide, maleimido, aziridinyl, alkylthio (disulfide), acrylo, α-haloalkylcarbonyl, boronate, hydrazide, semicarbazide, carbohydrazide, arylalkyl, heteroarylalkyl, cycloalkylalkyl, cycloalkenylalkyl, cycloheteroalkylalkyl, and cycloheteroalkenylalkyl. The term "optionally substituted" refers to a group that may or may not be substituted.

When the term "substituted" is used with reference to a cycloalkyl, cycloalkenyl, cycloheteroalkyl, cycloheteroalkenyl, aryl, or heteroaryl group, the term "substituted" herein refers to a group or groups being substituted with one or more substituents independently selected from the group consisting of hydroxy, oxo, nitro, trifluoromethyl, halogen, $C_{1-6}$ alkyl, $C_{2-6}$ alkenyl, $C_{2-6}$ alkynyl, $C_{6-10}$ aryl, 5–10 membered heteroaryl, $C_{1-6}$ alkoxy, $C_{6-10}$ ar($C_{1-6}$)alkoxy, $C_{1-6}$ alkylenedioxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl)amino, bis($C_{2-10}$ carboxyalkyl) amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ ar($C_{1-6}$)alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, or perfluoroethoxy.

Preferably, the term "substituted," when used with reference to a cycloalkyl, cycloalkenyl, cycloheteroalkyl, cycloheteroalkenyl, aryl, or heteroaryl group, refers to a group or groups being substituted with one or more substituents independently selected from the group consisting of $C_{1-4}$ alkyl, $C_{2-4}$ alkenyl, $C_{2-4}$ alkynyl, $C_{6-10}$ aryl, 5–10 membered heteroaryl, hydroxy, $C_{1-4}$ alkoxy, $C_{1-4}$ alkylenedioxy, halo, $C_{1-4}$ haloalkyl, $C_{1-4}$ alkylthio, thio, amino, mono($C_{1-4}$)alkylamino, and di($C_{1-4}$)alkylamino.

The term "fluorescence probe molecule" refers to a compound of Formula I. The compounds of Formula I, after excitement by light of a defined wavelength or defined range of wavelengths, are capable of emitting fluorescent energy. The fluorescence molecule or a compound may be capable of binding to an unfolded or denatured receptor.

The term "combinatorial library" refers to a plurality of molecules or compounds which are formed by combining, in every possible way for a given compound length, a set of chemical or biochemical building blocks which may or may not be related in structure. Alternatively, the term can refer to a plurality of chemical or biochemical compounds which are formed by selectively combining a particular set of chemical building blocks. Combinatorial libraries can be constructed according to methods familiar to those skilled in the art. For example, see Rapoport et al., *Immunology Today* 16:43–49 (1995); Sepetov, N. F. et al., *Proc. Natl. Acad. Sci. USA* 92:5426–5430 (1995); Gallop, M. A. et al., *J. Med. Chem.* 9:1233–1251 (1994); Gordon, E. M. et al., *J. Med. Chem.* 37:1385–1401 (1994); Stankova, M. et al., *Peptide Res.* 7:292–298 (1994); Erb, E. et al., *Proc. Natl. Acad. Sci. USA* 91:11422–11426 (1994); DeWitt, S. H. et al., *Proc. Natl. Acad. Sci. USA* 90:6909–6913 (1993); Barbas, C. F., et al., *Proc. Natl. Acad. Sci. USA* 89:4457–4461 (1992); Brenner, S. et al. *Proc. Natl. Acad. Sci. USA* 89:5381–5383 (1992); Lam, K. S. et al., *Nature* 354:82–84 (1991); Devlin, J. J. et al., *Science* 245:404–406 (1990); Cwirla, S. E. et al., *Proc. Natl. Acad. Sci. USA* 87:6378–6382 (1990); Scott, J. K. et al., *Science* 249:386–390 (1990). Preferably, the term "combinatorial library" refers to a directed diversity chemical library, as set forth in U.S. Pat. No. 5,463,564. Regardless of the manner in which a combinatorial library is constructed, each molecule or compound in the library is catalogued for future reference.

The term "compound library" refers to a plurality of molecules or compounds which were not formed using the combinatorial approach of combining chemical or biochemical building blocks. Instead, a compound library is a plurality of molecules or compounds which are accumulated and are stored for use in future ligand-receptor binding assays. Each molecule or compound in the compound library is catalogued for future reference.

The terms "multiplicity of molecules," "multiplicity of compounds," and "multiplicity of containers" refer to at least two molecules, compounds, or containers.

The term "multi-variable" refers to more than one experimental variable.

The term "screening" refers to the testing of a multiplicity of molecules or compounds for their ability to bind to a target molecule which is capable of denaturing and/or unfolding. Screening is a repetitive, or iterative, process, in which molecules are tested for binding to a target molecule (e.g., a protein receptor) in a thermal shift assay. For example, if none of a subset of molecules from the multiplicity of molecules (e.g., a combinatorial library) bind to the target molecule, then a different subset is tested for binding in a thermal shift assay.

The term "ranking" refers to the ordering of the affinities of a multiplicity of molecules or compounds for a target molecule, according to the ability of the molecule or compound to shift the thermal unfolding information (e.g., thermal unfolding $T_m$) obtained for the target molecule, relative to the thermal unfolding information of the target molecule in the absence of any molecule or compound.

The term "high-throughput" encompasses screening activity in which human intervention is minimized, and automation is maximized. For example, high-throughput screening involves automated pipetting, mixing, and heating, software-controlled generation of thermal unfolding information, and software-controlled comparisons of thermal unfolding information. Alternatively, a high-throughput method is one in which hundreds of compounds can be screened per 24 hour period by a single individual operating a single suitable apparatus.

The phrase "performed automatically" means that at least some aspects of the screening process are performed by a machine, and optionally are computer-controlled.

The term "ranking" also refers to the ordering of the efficacies of a multiplicity of biochemical conditions in optimizing protein stabilization, protein folding, protein crystallization, or protein shelf life. In the context of optimization of protein stabilization, optimization of protein folding, optimization of protein crystallization, and optimization of protein shelf life, the term "ranking" refers to the ordering of the efficacies of one or more combinations of biochemical conditions to shift the thermal unfolding information (e.g., thermal unfolding $T_m$) obtained for the target molecule, relative to the thermal unfolding information of the target molecule under a reference set of conditions.

As discussed above, ranking molecules, compounds, or biochemical conditions according to a change in the $T_m$ is preferable. Alternatively, molecules, compounds, or biochemical conditions can be ranked for their ability to stabilize a target molecule according to the change in entire thermal unfolding curve.

As used herein, the terms "protein" and "polypeptide" are synonymous. For proteins or peptides, the term "unfolding" encompasses any change in structure due to heating. For example, the term "unfolding" refers to the transition of from the liquid crystalline state to the molten globule state. In the molten globule state, tertiary and quaternary structure has been altered, relative to the native state of the protein, and at least some secondary structure remains intact. The term "unfolding" also encompasses loss of crystalline ordering of amino acid side-chains, secondary, tertiary or quaternary structure. The term "unfolding" also encompasses formation of a random coil.

The terms "folding," "refolding," and "renaturing" refer to the acquisition of the correct amino acid side-chain ordering, secondary, tertiary, or quaternary structure, of a protein or a nucleic acid, which affords the full chemical and biological function of the biomolecule.

The term "denatured protein" refers to a protein which has been treated to remove native amino acid side-chain ordering, secondary, tertiary, or quaternary structure. The term "native protein" refers to a protein which possesses the degree of amino acid side-chain ordering, secondary, tertiary or quaternary structure that provides the protein with full chemical and biological function. A native protein is one which has not been heated and has not been treated with a chemical unfolding agent, such as urea.

For nucleic acids, the term "unfolding" refers to the loss of secondary, tertiary, and/or quaternary structure through unfolding, uncoiling, untwisting or loss of helical structure. The loss of double- or triple-helical structure through the interruption of base-paring is an example of unfolding of a nucleic acid.

The terms "unfolded nucleic acid" and "denatured nucleic acid" refer to a nucleic acid which has been treated to remove folded, coiled, helical, or twisted structure. Unfolding of a triple-stranded nucleic acid complex is complete when the third strand has been removed from the two complementary strands. Unfolding of a double-stranded DNA is complete when the base pairing between the two complementary strands has been interrupted and has resulted in single-stranded DNA molecules that have assumed a random form. Unfolding of single-stranded RNA is complete when intramolecular hydrogen bonds have been interrupted, and the RNA has assumed a random, non-hydrogen bonded form.

An "unfolding curve" is a plot of the physical change associated with the unfolding of a protein as a function temperature, denaturant concentration, pressure, and other biochemical and physiochemical parameters. An unfolding curve can be generated digitally or by plotting on paper or a computer screen. A "thermal unfolding curve" is a plot of the physical change associated with the unfolding of a protein or a nucleic acid as a function of temperature. See, for example, Davidson et al., *Nature Structure Biology* 2:859 (1995); and Clegg, R. M. et al., *Proc. Natl. Acad. Sci. USA* 90:2994–2998 (1993). A thermal unfolding curve can be generated digitally or by plotting on paper or a computer screen. Preferably, a thermal unfolding curve is generated digitally.

The "midpoint temperature, $T_m$," is the temperature midpoint of a thermal unfolding curve. At the temperature midpoint, $T_m$, one half of the target molecules in a sample are unfolded, and one half of the target molecules in the sample remain folded. The $T_m$ can be readily determined using methods well known to those skilled in the art. See, for example, Weber, P. C. et al., *J. Am. Chem. Soc.* 116: 2717–2724 (1994); Clegg, R. M. et al., *Proc. Natl. Acad. Sci. USA* 90:2994–2998 (1993). Preferably, the $T_m$ is extracted digitally from a digital thermal unfolding curve.

The phrase "thermal unfolding information" is information relating to target molecule unfolding in response to heating. For example, a thermal unfolding curve is one kind of thermal unfolding information. A thermal unfolding curve can be plotted on a computer screen, or on paper. Preferably, a thermal unfolding curve is generated digitally, using computer software, and may then be visualized on a computer screen. More preferably, thermal unfolding information is thermal unfolding $T_m$. A digitally generated thermal unfolding curve need not be printed or displayed in order for the thermal unfolding $T_m$ to be extracted from the digitally generated curve. Most preferably, the thermal unfolding $T_m$ is digitally extracted from a digitally generated thermal unfolding curve.

When thermal unfolding information is generated digitally, five fitting parameters are evaluated: (1) $y_f$, the pre-transitional fluorescence for the native protein; (2) $y_u$, the post-transitional fluorescence for the unfolded protein; (3) $T_m$, the temperature at the midpoint for the unfolding transition; (4) $\Delta H_u$, the van't Hoff unfolding enthalpy change; and (5) $\Delta C_{pu}$, the change in heat capacity upon protein unfolding. The non-linear least squares curve fitting can be performed using a suitable software, such as KALEIDAGRAPH™ 3.0 software (Synergy Software, Reading Pa.), which allows the five fitting parameters to float while utilizing Marquardt methods for the minimization of the sum of the squared residuals. The temperature midpoint $T_m$ is extracted from the digitally generated thermal unfolding information.

As used herein, the term "temperature profile" refers to a change in temperature over time. The term "temperature profile" encompasses continuous upward or downward changes in temperature, both linear and non-linear changes. The term also encompasses any stepwise temperature change protocols, including protocols characterized by incremental increases or decreases in temperature during which temperature increases or decreases are interrupted by periods during which temperature is maintained constant.

The term "lead molecule" refers to a molecule or compound, from a combinatorial library, which displays relatively high affinity for a target molecule. The terms "lead compound" and "lead molecule" are synonymous. The term "relatively high affinity" relates to affinities in the $K_d$ range of from $10^{-4}$ to $10^{-15}$ M.

The term "target molecule" encompasses peptides, proteins, nucleic acids, and other receptors. The term encompasses both enzymes, and proteins which are not enzymes. The term encompasses monomeric and multimeric proteins. Multimeric proteins may be homomeric or heteromeric. The term encompasses nucleic acids comprising at least two nucleotides, such as oligonucleotides. Nucleic acids can be single-stranded, double-stranded, or triple-stranded. The term encompasses a nucleic acid which is a synthetic oligonucleotide, a portion of a recombinant DNA molecule, or a portion of chromosomal DNA. The term target molecule also encompasses portions of peptides, proteins, and other receptors which are capable of acquiring secondary, tertiary, or quaternary structure through folding, coiling or twisting. The target molecule may be substituted with substituents including, but not limited to, cofactors, coenzymes, prosthetic groups, lipids, oligosaccharides, or phosphate groups.

The terms "target molecule" and "receptor" are synonymous.

Examples of target molecules are included, but not limited to those disclosed in Faisst, S. et al., *Nucleic Acids Research* 20:3–26 (1992); Pimentel, E., Handbook of Growth Factors, Volumes I–III, CRC Press, (1994); Gilman, A. G. et al., *The Pharmacological Basis of Therapeutics*, Pergamon Press (1990); Lewin, B., *Genes V*, Oxford University Press (1994); Roitt, I., *Essential Immunology*, Blackwell Scientific Publ. (1994); Shimizu, Y., *Lymphocyte Adhesion Molecules*, R G Landes (1993); Hyams, J. S. et al., *Microtubules*, Wiley-Liss (1995); Montreuil, J. et al., *Glycoproteins, Elsevier* (1995); Woolley, P., *Lipases. Their Structure Biochemistry and Applications*, Cambridge University Press (1994); Kurjan, J., *Signal Transduction: Prokaryotic and Simple Eukaryotic Systems*, Academic Press (1993); Kreis, T., et al., *Guide Book to the Extra Cellular Matrix and Adhesion Proteins*, Oxford University Press (1993); Schlesinger, M. J., *Lipid Modifications of Proteins*, CRC Press (1992); Conn, P. M., *Receptors: Model Systems and Specific Receptors*, Oxford University Press (1993); Lauffenberger, D. A. et al., *Receptors. Models For Binding Trafficking and Signaling*, Oxford University Press (1993); Webb, E. C., *Enzyme Nomenclature*, Academic Press (1992); Parker, M. G., *Nuclear Hormone Receptors, Molecular Mechanisms, Cellular Functions Clinical Abnormalities*, Academic Press Ltd. (1991); Woodgett, J. R., *Protein Kinases*, Oxford University Press (1995); Balch, W. E. et al., *Methods in Enzymology*, Vol. 257, Pt. C: "Small GTPases and Their Regulators: Proteins Involved in Transport," Academic Press (1995); *The Chaperonins*, Academic Press (1996); Pelech, L., *Protein Kinase Circuitry in Cell Cycle Control*, R G Landes (1996); Atkinson, *Regulatory Proteins of the Complement System*, Franklin Press (1992); Cooke, D. T. et al., *Transport and Receptor Proteins of Plant Membranes: Molecular Structure and Function*, Plenum Press (1992); Schumaker, V. N., *Advances in Protein Chemistry: Lipoproteins, Apolipoproteins, and Lipases*, Academic Press (1994); Brann, M., *Molecular Biology of G-Protein-Coupled Receptors: Applications of Molecular Genetics to*

*Pharmacology*, Birkhauser (1992); Konig, W., *Peptide and Protein Hormones. Structure, Regulations, Activity-A Reference Manual*, VCH Publ. (1992); Tuboi, S. et al., *Post-Translational Modification of Proteins*, CRC Press (1992); Heilmeyer, L. M., *Cellular Regulation by Protein Phosphorylation*, Springer-Verlag (1991); Takada, Y., *Integrin: The Biological Problem*, CRC Press (1994); Ludlow, J. W., *Tumor Suppressors: Involvement in Human Disease, Viral Protein Interactions, and Growth Regulation*, R G Landes (1994); Schlesinger, M. J., *Lipid Modification of Proteins*, CRC Press (1992); Nitsch, R. M., *Alzheimer's Disease: Amyloid Precursor Proteins, Signal Transduction, and Neuronal Transplantation*, New York Academy of Sciences (1993); Cochrane, C. G., et al., *Cellular and Molecular Mechanisms of Inflammation*, Vol. 3*: Signal Transduction in Inflammatory Cells*, Part A, Academic Press (1992); Gupta, S. et al., *Mechanisms of Lymphocyte Activation and Immune Regulation IV: Cellular Communications*, Plenum Press (1992); Authi, K. S. et al., *Mechanisms of Platelet Activation and Control*, Plenum Press (1994); Grunicke, H., *Signal Transduction Mechanisms in Cancer*, R G Landes (1995); Latchman, D. S., *Eukaryotic Transcription Factors*, Academic Press (1995).

The term "molecule" refers to the compound which is tested for binding affinity for the target molecule. This term encompasses chemical compounds of any structure, including, but not limited, to nucleic acids and peptides. More specifically, the term "molecule" encompasses compounds in a compound library or a combinatorial library.

The term "fluorescence" encompasses the release of fluorescent energy. Less broadly, the term "fluorescence" refers to fluorescent emission, the rate of change of fluorescence over time (i.e., fluorescence lifetime), fluorescence polarization, fluorescence anisotropy, and fluorescence resonance energy transfer. See Eftink, M. R., *Biophysical J.* 66:482–501 (1994).

The term "contacting a target molecule" refers broadly to placing the target molecule in solution with the molecule to be screened for binding or with the condition(s) to be tested for stabilizing the target molecule. Less broadly, contacting refers to the turning, swirling, shaking or vibrating of a solution of the target molecule and the molecule to be screened for binding. More specifically, contacting refers to the mixing of the target molecule with the molecule to be tested for binding. Mixing can be accomplished, for example, by repeated uptake and discharge through a pipette tip, either manually or using an automated pipetting device. Preferably, contacting refers to the equilibration of binding between the target molecule and the molecule to be tested for binding. Contacting can occur in the container, infra, or before the target molecule and the molecule to be screened are placed in the container.

The target molecule may be contacted with a nucleic acid prior to being contacted with the molecule to be screened for binding. The target molecule may be complexed with a peptide prior to being contacted with the molecule to be screened for binding. The target molecule may be phosphorylated or dephosphorylated prior to being contacted with the molecule to be screened for binding.

A carbohydrate moiety may be added to the target molecule before the target molecule is contacted with the molecule to be screened for binding. Alternatively, a carbohydrate moiety may be removed from the target molecule before the target molecule is contacted with the molecule to be screened for binding.

The term "container" refers to any vessel or chamber in which the receptor and molecule to be tested for binding can be placed. The term "container" encompasses reaction tubes (e.g., test tubes, microtubes, vials, etc.). In the methods of the present invention, the term "container" preferably refers to a well in a multiwell microplate or multiwell microtiter plate.

The term "sample" refers to the contents of a container.

The terms "spectral emission," "thermal change," and "physical change" encompass the release of energy in the form of light or heat, the absorption of energy in the form or light or heat, changes in turbidity and changes in the polar properties of light. Specifically, the terms refer to fluorescent emission, fluorescent energy transfer, absorption of ultraviolet or visible light, changes in the polarization properties of light, changes in the polarization properties of fluorescent emission, changes in the rate of change of fluorescence over time (i.e., fluorescence lifetime), changes in fluorescence anisotropy, changes in fluorescence resonance energy transfer, changes in turbidity, and changes in enzyme activity. Preferably, the terms refer to fluorescence, and more preferably to fluorescence emission. Fluorescence emission can be intrinsic to a protein or can be due to a fluorescence reporter molecule. The use of fluorescence techniques to monitor protein unfolding is well known to those of ordinary skill in the art. For example, see Eftink, M. R., *Biophysical J.* 66:482–501 (1994).

The fluorescence microplate thermal shift assay is disclosed in U.S. Pat. No. 6,020,141, issued Feb. 1, 2000.

The term "carrier" encompasses a platform or other object, of any shape, which itself is capable of supporting at least two containers. The carrier can be made of any material, including, but not limited to glass, plastic, or metal. Preferably, the carrier is a multiwell microplate. The terms microplate and microtiter plate are synonymous. The carrier can be removed from the heating element. In the present invention, a plurality of carriers are used. Each carrier holds a plurality of wells.

The term "biochemical conditions" encompasses any component of a physical, chemical, or biochemical reaction. Specifically, the term refers to conditions of temperature, pressure, protein concentration, pH, ionic strength, salt concentration, time, electric current, potential difference, concentrations of cofactor, coenzyme, oxidizing agents, reducing agents, detergents, metal ion, ligands, or glycerol.

The term "efficacy" refers to the effectiveness of a particular set of biochemical conditions in facilitating the refolding or renaturation of an unfolded or denatured protein.

The term "reference set of conditions" refers to a set of biochemical conditions under which thermal unfolding information for a target molecule is obtained. Thermal unfolding information obtained under conditions different than the reference conditions is compared to the thermal unfolding information obtained for the target molecule under reference conditions.

The term "polarimetric measurement" relates to measurements of changes in the polarization of fluorescence.

The term "collection" refers to a pool or a group of at least two molecules to be tested for binding to a target molecule or receptor in a single container.

A "host" is a bacterial cell that has been transformed with recombinant DNA for the purpose of expressing protein which is heterologous to the host bacterial cell.

The fluorescence thermal shift assay is based on the ligand-dependent change in thermal unfolding information (e.g., the $T_m$) of a target receptor, such as a protein or a nucleic acid. When heated over a range of temperatures, a receptor will unfold. By plotting the degree of unfolding as a function of temperature, one obtains a thermal unfolding curve for the receptor. Naturally, a thermal unfolding curve can be generated digitally, using computer software. The temperature midpoint $T_m$ is the temperature at which one half of the receptor molecules are unfolded, and one half of the molecules remain folded.

Ligand binding stabilizes the receptor (Schellman, J., *Biopolymers* 14:999–1018 (1975)). The extent of binding and the free energy of interaction follow parallel courses as a function of ligand concentration (Schellman, J., Biophysical Chemistry 45:273–279 (1993); Barcelo, F. et al., *Chem. Biol. Interactions* 74:315–324 (1990)). As a result of stabilization by ligand, more energy (heat) is required to unfold the receptor. Thus, ligand binding shifts the thermal unfolding information (e.g., the $T_m$). This property can be exploited to determine whether a ligand binds to a receptor: a change, or "shift", in the thermal unfolding information, and thus means that the ligand binds to the receptor.

Uses of Compounds

Compounds of the present invention are useful as fluorescence probe molecules in applications wherein fluorescence probes are known to be useful. In using a compound of Formula I as fluorescence probe molecule, the compound of Formula I is added to a sample to be probed. The sample comprising the compound of Formula I is then exposed to a light source. Said light source produces light that is limited to a range of wavelengths. The range of wavelengths is between about 200 and about 600 nanometers (nm), preferably between about 250 and about 500 nm, most preferably between about 300 and about 400 nm. Upon exposure to said light source, the compound of Formula I undergoes fluorescence and emits fluorescent energy. Preferably, said fluroescent energy is fluorescent light energy. Said emitted fluorescent energy is detected using methods well known in the art. The intensity and wavelength of said emitted fluorescent energy provides information about the sample. Said emitted fluorescent energy preferably has a range of wavelengths between about 300 and about 800 nm, preferably between about 400 and about 700 nm, preferably between about 450 and about 700 nm. In particular, compounds of Formula I are useful as fluorescence probe molecules in fluorescent thermal shift assays. Fluorescence thermal shift assays are fully described in U.S. Pat. No. 6,020,141, which is hereby fully incorporated by reference.

Another aspect of the present invention provides for a use of compounds of Formula I in a method for ranking the affinity of each of a multiplicity of different molecules for a target molecule which is capable of unfolding due to a thermal change, said method comprising (a) contacting the target molecule with one molecule of a multiplicity of different molecules, in the presence of a compound of Formula I, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule in the absence of any of the molecules in the multiplicity of different molecules; and (f) ranking the affinities of each of the molecules according to the difference in the thermal unfolding information between the target molecule in each of the containers and the target molecule in the absence of any of the molecules in the multiplicity of different molecules.

Another aspect of the present invention provides for a use of the compounds of Formula I in a multi-variable method for ranking the affinity of a combination of two or more of a multiplicity of different molecules for a target molecule which is capable of unfolding due to a thermal change, said method comprising: (a) contacting the target molecule with a combination of two or more different molecules of the multiplicity of different molecules, in the presence of a compound of Formula I, in each of a multiplicity of containers; (b) simultaneously heating the multiplicity of containers; (c) measuring in the fluorescence in each of the containers; (d) generating thermal unfolding information for the target molecule as a function of temperature in each of the containers; (e) comparing the thermal unfolding information obtained for each of the containers to (i) the thermal unfolding information obtained for each of the other containers, and (ii) the thermal unfolding information obtained for the target molecule in the absence of any of the two or more different molecules; and (f) ranking the affinities of the combinations of the two or more of the multiplicity of different molecules according to the difference in the thermal unfolding information between the target molecule in each of the containers and the thermal unfolding information obtained for the target molecule in the absence of any of the molecules in the multiplicity of different molecules.

Another aspect of the present invention provides for a use of compounds of Formula I in a method for assaying a collection of a multiplicity of different molecules for a molecule which binds to a target molecule which is capable of unfolding due to a thermal change, said method comprising: (a) contacting the target molecule with a collection of at least two molecules of the multiplicity of different molecules, in the presence of a compound of Formula I, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule in the absence of any of the multiplicity of different molecules; and (f) ranking the affinities of the collections of different molecules according to the difference in the thermal unfolding information between the target molecule in each of the containers and the thermal unfolding information obtained for the target molecule in the absence of any of the molecules in the multiplicity of different molecules; (g) selecting the collection of different molecules which contains a molecule with affinity for the target molecule; (h) dividing the selected collection into smaller collections of molecules in each of a multiplicity of containers; and (i) repeating the above steps (a)–(h) until a single molecule, from the multiplicity of different molecules, is identified.

Another aspect of the present invention provides for a use of comopunds of Formula I in a multi-variable method for ranking the efficacy of one or more of a multiplicity of different biochemical conditions for stabilizing a target molecule which is capable of unfolding due to a thermal change, said method comprising: (a) contacting the target molecule with one or more of the multiplicity of biochemical conditions, in the presence of a compound of Formula I, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule under a reference set of biochemical conditions; and (f) ranking the efficacies of each of the biochemical conditions for each of the containers according to the difference in the thermal unfolding information between the target molecule for each of the containers and the target molecule under the reference set of biochemical conditions.

Another aspect of the present invention provides for a use of comopunds of Formula I in a multi-variable method for optimizing the shelf life of a target molecule which is capable of unfolding due to a thermal change, said method comprising: (a) contacting the target molecule with one or more of a multiplicity of different molecules or different biochemical conditions, in the presence of a compound of Formula I, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule under a reference set of biochemical conditions; and (f) ranking the efficacies of each of the biochemical conditions for each of the containers according to the difference in the thermal unfolding information between the target molecule for each of the containers and the target molecule under the reference set of biochemical conditions.

Another aspect of the present invention provides for a use of comopunds of Formula I in a multi-variable method for ranking the efficacies of one or more of a multiplicity of different biochemical conditions to facilitate the refolding or renaturation of a sample of a denatured or unfolded protein, said method comprising: (a) placing one of the refolded protein samples, in the presence of a compound of Formula I, in each of a multiplicity of containers, wherein each of the refolded protein samples has been previously refolded or renatured according to one or more of the multiplicity of conditions; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule under a reference set of biochemical conditions; and (f) ranking the efficacies of each of the biochemical conditions for each of the containers according to the difference in the thermal unfolding information between the target molecule for each of the containers and the target molecule under the reference set of biochemical conditions.

Another aspect of the present invention provides for a use of comopunds of Formula I in a multi-variable method for ranking the efficacy of one or more of a multiplicity of different biochemical conditions for facilitating the crystallization of a protein which is capable of unfolding due to a thermal change, said method comprising: (a) contacting the protein with one or more of the multiplicity of different biochemical conditions, in the presence of a compound of Formula I, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule under a reference set of biochemical conditions; and (f) ranking the efficacies of each of the biochemical conditions for each of the containers according to the difference in the thermal unfolding information between the target molecule for each of the containers and the target molecule under the reference set of biochemical conditions.

Compounds of the present invention may also be used in an improved method for generating lead compounds. After a compound or a combinatorial library of compounds has been screened using the thermal shift assay, compounds which bind to the target receptor are chemically modified to generate a second library of compounds. This second library is then screened using the thermal shift assay. This process of screening and generating a new library continues until compounds that bind to the target receptor with affinities in the $K_d$ range of from $10^{-4}$ to $10^{-15}$ Mare obtained.

A fluorescence imaging system can be used to monitor the thermal unfolding of a target molecule or a receptor. Fluorescence imaging systems are well known to those skilled in the art. For example, the AlphaImager™ Gel Documentation and Analysis System (Alpha Innotech, San Leandro, Calif.) employs a high performance charge coupled device camera with 768×494 pixel resolution. The charge coupled device camera is interfaced with a computer and images are analyzed with Image analysis software™. The CHEMIIMAGER™ (Alpha Innotech) is a cooled charge coupled device that performs all of the functions of the ALPHAIMAGER™ and in addition captures images of chemiluminescent samples and other low intensity samples. The CHEMIIMAGER™ charge coupled device includes a Pentium processor (1.2 Gb hard drive, 16 Mb RAM), AlphaEase™ analysis software, a light tight cabinet, and a UV and white light trans-illuminator. For example, the MRC-1024 UV/Visible Laser Confocal Imaging System (BioRad, Richmond, Calif.) facilitates the simultaneous imaging of more than one fluorophore across a wide range of illumination wavelengths (350 to 700 nm). The Gel Doc 1000 Fluorescent Gel Documentation System (BioRad, Richmond, Calif.) can clearly display sample areas as large as 20×20 cm, or as small as 5×4 cm. At least two 96 well microplates can fit into a 20×20 cm area. The Gel Doc 1000 system also facilitates the performance of time-based experiments.

A fluorescence thermal imaging system can be used to monitor receptor unfolding in a microplate thermal shift assay. In this embodiment, a plurality of samples is heated simultaneously at temperatures between 25 to 110° C. A fluorescence reading is taken for each of the plurality of samples simultaneously. For example, the fluorescence in each well of a 96 or a 384 well microplate can be monitored simultaneously. Alternatively, fluorescence readings can be taken continuously and simultaneously for each sample. At lower temperatures, all samples display a low level of fluorescence. As the temperature is increased, the fluorescence in each sample increases. Wells which contain ligands which bind to the target molecule with high affinity shift the thermal unfolding $T_m$ to a higher temperature. As a result, wells which contain ligands which bind to the target molecule with high affinity fluoresce less, at a given temperature above the $T_m$ of the target molecule in the absence of any ligands, than wells which do not contain high-affinity ligands. If the samples are heated in incremental steps, the fluorescence of all of the plurality of samples is simultaneously imaged at each heating step. If the samples are heated continuously, the fluorescence of all of the plurality of samples is simultaneously imaged during heating.

A fluorescence thermal shift assay can be performed in a volume of 100 µL. For the following reasons, however, it is preferable to perform a thermal shift assay in a volume of 1–10 µL. First, approximately 10- to 100-fold less protein is required for the miniaturized assay. Thus, only ~4 to 40 pmole of protein are required (0.1 µg to 1.0 µg for a 25 kDa protein) for the assay (i.e., 1 to 10 µL working volume with a target molecule concentration of about 1 to about 4 µM). Thus, as little as 1 mg of protein can be used to conduct 1,000 to 10,000 assays in the miniaturized format. This is particularly advantageous when the target molecule is available in minute quantities.

Second, approximately 10- to 100-fold less ligand is required for the miniaturized assay. This advantage is very important to researchers when screening valuable combinatorial libraries for which library compounds are synthesized in minute quantities. In the case of human α-thrombin, the ideal ligand concentration is about 50 µM, which translates into 25–250 pmoles of ligand, or 10–100 ng (assuming a MW of 500 Da) of ligand per assay in the miniaturized format.

Third, the smaller working volume allows the potential of using larger arrays of assays because the miniaturized assay can fit into a much smaller area. For example, a 384 well (16×24 array) or 864 well (24×36 array) plates have the same dimensions as the 96 well plates (8.5×12.5 cm). The 384 well plate and the 864 well plate allows the user to perform 4 and 9 times as many assays, respectively, as can be performed using a 96 well plate.

Alternatively, 1536 well plates (32×48 arrays; Matrix Technologies Corp.) can be used. A 1536 well plate will facilitate sixteen times the throughput afforded by a 96 well plate. Thus, using the 1536 well plate configuration, the assay speed can be increased by about 16 times, relative to the speed at which the assay can be performed using the 96 well format. The 8×12 assay array arrangement (in a 96-well plate) facilitates the performance of 96 assays/hr, or about 2300 assays/24 hours. The 32×48 array assay arrangement facilitates the performance of about 1536 assays hr., or about 37,000 assays/24 hours can be performed using a 32×48 assay array configuration.

Alternatively, microplates containing more than 1536 wells per plate can be used in the methods of the present invention.

The assay volume can be 1–100 µL. Preferably, the assay volume is 1–50 µL. More preferably, the assay volume is 1–25 µL. More preferably still, the assay volume is 1–10 µL. More preferably still, the assay volume is 1–5 µL. More preferably still, the assay volume is 5 µL. Most preferably, the assay volume is 1 µL or 2 µL.

Preferably, the assay is performed in V-bottom polycarbonate plates or polycarbonate dimple plates. A dimple plate is a plate that contains a plurality of round-bottom wells that hold a total volume of 15 µL.

In the methods of the present invention, generation of thermal unfolding information can further comprise determining a thermal unfolding $T_m$, and the comparing step comprises comparing the $T_m$ for the target molecule in each container to (i) the $T_m$ for the target molecule in each of the other containers, and to (ii) the $T_m$ obtained for the target molecule in the absence of any of the different molecules or obtained under a reference set of biochemical conditions, and wherein the ranking step comprises ranking the efficacies of the multiplicity of different molecules or the multiplicity of different biochemical conditions according to differences in the $T_m$.

In the methods of the present invention, the measuring step comprise contacting the protein with the one or more different molecules or different biochemical conditions, in the presence of a molecule of Formula I present in each of the multiplicity of containers, and wherein the measuring step comprises exciting the molecule of Formula I, in each of the multiplicity of containers with light; and measuring the fluorescence from each of the multiplicity of containers.

In the methods of the present invention, when the target molecule is a double-stranded oligonucleotide, one strand contains a donor fluorophore and the other strand of the oligonucleotide contains an acceptor fluorophore. The contacting step can comprise contacting the oligonucleotide with the multiplicity of different molecules, or with the multiplicity of different biochemical conditions, in each of the multiplicity of containers, and wherein the measuring step exciting the donor fluorophore, in each of the multiplicity of containers, with light; and measuring the fluorescence from the acceptor fluorophore in each of the multiplicity of containers In the methods of the present invention, fluorescence can be measured in all of the containers simultaneously. Alternatively, fluorescence can be measured in a subset of the containers simultaneously. Alternatively, fluorescence can be measured one container at a time.

One alternative to taking fluorescence readings over a temperature range around the $T_m$ of the therapeutic target to obtain a full thermal unfolding curve for the ligand/target complex, in order to identify shifts in $T_m$, is to perform the assay at a single temperature near the $T_m$ of the target molecule. In this embodiment, samples that fluorescence less, relative to a control sample (containing a target molecule, but no candidate ligand) indicate that the candidate ligand binds to the target molecule.

In this embodiment, the fluorescence associated with the thermal unfolding of a target molecule resulting from heating is determined by generating thermal unfolding information for the target molecule as a function of temperature over a range of one or more discrete or fixed temperatures. The fluorescence associated with thermal unfolding, is measured. The fluorescence at the discrete or fixed temperature for the target molecule in the absence of any ligand is noted. The fluorescence in the presence of each of a multiplicity of different molecules, for example, combinatorial compounds, is measured. The fluorescence associated with thermal unfolding of the target molecule in the presence of each of the multiplicity of molecules is compared to fluorescence obtained for the target molecule at the discrete or fixed temperature in the absence of any of the multiplicity of different molecules. The affinities of the multiplicity of different molecules are ranked according to the change in the fluorescence.

The discrete or fixed temperature at which the fluorescence is measured can be any temperature that is useful for discriminating shifts in thermal stability. Preferably, the discrete or fixed temperature is the midpoint temperature $T_m$ for the target molecule in the absence of any of the multiplicity of different molecules tested for binding to the target molecule.

The methods of the present invention are not limited to assaying ligand-protein interactions. The methods of the present invention can be used to rapidly assay any multivariable system related to protein stabilization. For example, the methods of the present invention can be used to simultaneously assay the binding of more than one compound or ligand to a target molecule. Using this approach, the additive effect of multiple-ligand binding can be assessed. Positive and negative cooperativity can be determined. To accomplish this method, fluorescence thermal shift assays are performed for a target molecule, such as a protein, in the absence of any ligands, in the presence of a single ligand, and in the presence of two or more ligands. Thermal unfolding information is generated for the protein alone and for each combination of protein and ligand(s). The midpoint temperature $T_m$ is then determined for the protein alone and for each combination. Each $T_m$ is then compared to each of the other $T_m$'s for the other combinations. Alternatively, an unfolding curve is generated for the protein alone and for each combination, and each thermal unfolding curve is compared to each of the other thermal unfolding curves. In either of these manners, the additive contribution of more than one ligand to binding interaction or to protein stability can be determined.

In a similar fashion, the additive contributions of one or more biochemical conditions to protein stability can be determined. Thus, the present invention can be used to rapidly identify biochemical conditions that optimize protein stabililty, and hence shelf-life of a protein. Further, the methods of the present invention can be used to rank the efficacies of various biochemical conditions for refolding or renaturing an unfolded or denatured protein. This embodiment addresses the need in the art for a reliable method for screening for effective refolding or renaturing conditions.

For example, expression of recombinant DNA in a bacterial cell usually results in the sequestration of recombinant protein into bacterial inclusion bodies (Marston, F. A. O., *Biochem. J.* 240:1–12 (1986)). Although other expression systems can be used instead of bacterial expression systems, expression in bacterial cells remains the method of choice for the high-level production of recombinant proteins (Rudolph, R., *Protein Engineering: Principles and Practices*, pp. 283–298, John Wiley & Sons (1995)). In many cases, recovery of recombinant protein requires that protein be isolated from inclusion bodies. Protein purification from inclusion bodies process necessitates the denaturation of recombinant protein. As a result, recombinant protein must be renatured or refolded under conditions suitable to generate the protein in its native, fully functional form.

In each of these cases, denatured protein must be renatured or refolded in order to be useful for further study or use. Unfortunately, one cannot easily predict the exact conditions under which a given protein or fragment of the protein should be renatured. Each protein is different. One must always resort to testing a number of different combinations of renaturing conditions before one can know which set of conditions is optimal. Thus, it is desirable to have a reliable and rapid method for ranking the efficacies of various renaturing conditions.

Recombinant DNA technology has allowed the biosynthesis of a wide variety of heterologous polypeptides of interest in relatively large quantities through the recruitment of the bacterial protein expression apparatus. However, the promise of cheap and abundant supplies of correctly folded rare human proteins of high therapeutic value expressed in *E. coli* has foundered due to the overwhelmingly predominant aggregation of unfolded or partially unfolded target proteins into insoluble protein inclusion bodies. For recent reviews, see Rudolph, R., & Lilie, H., *FASEB J.* 10:49–56 (1995); Sadana, A., *Biotechnology & Bioengineering* 48:481–489 (1995); Jaenicke, R., *Phil. Trans. Royal Soc. London Ser. B-Biol. Sci.* 348:97–105 (1995)). Reasons for the prevailing self aggregation reaction in *E. coli* have centered on the relatively high concentration of the heterologous protein (as high as 30% of the weight of the cell) found to various degrees in partially unfolded states. Thus, at the elevated protein concentrations of an overexpressing *E. coli* strain, the exposed hydrophobic residues of unfolded proteins are more likely to encounter other molecules with similarly exposed groups (inter-molecular reaction) than they are to sample self collapsed polypeptide conformations where these hydrophobic residues are packed in a proper orientation (intra-molecular transition state) for proceeding to the fully folded native state (see FIG. 26). From this perspective, the insoluble protein inclusion bodies are seen as kinetically trapped side reaction products that thwart the preferred protein folding process.

Techniques for isolating inclusion bodies, purifying recombinant protein from inclusion bodies, and techniques for refolding or renaturing protein are well known to those skilled in the art. For example, see Sambrook, J. et al., *Molecular Cloning: a Laboratory Manual*, Cold Spring Harbor Laboratory Press (1989), pp. 17.37–17.41; Rudolph, R., et al, *FASEB J.* 10:49–56 (1995).

Another impediment to producing large quantities of correctly folded proteins in *E. coli* is that the reducing redox potential of the *E. coli* cytosol impedes the formation of disulfide bonds in vivo. The formation of disulfide bonds is an important co- and post-translational event in the biosynthesis of many extracellular proteins that is often coupled to protein folding. In addition, the cis-trans proline isomerization reaction has been demonstrated to be a rate determining step for correct folding of certain proteins (Lin, L.-N., & Brandts, J. F., *Biochemistry* 22:564–573 (1983)). As a result, partially folded intermediates accumulate in sufficient quantity in vivo that they aggregate and precipitate into protein masses.

Cells employ a class of host proteins called molecular chaperonins that assist in vivo protein folding by apparently preventing many of the unproductive side reactions discussed above with regard to inclusion body formation, i.e., aggregation and improper disulfide bond formation. However, the *E. coli* chaperonin machinery, which is comprised in part by the proteins, GroEL and GroES, presumably becomes overwhelmed by massive overexpression. Despite many attempts to correct this chaperonin deficit by co-expression of molecular chaperonins with the protein of interest (Rudolph, R., & Lilie, H., *The FASEB J* 10:49–56 (1995)) positive results have been reported in only one case (Goloubinoff, P., et al., *Nature* 342:884–889 (1989)).

Two hypotheses have been promoted to explain how GroEL and GroES assist in vivo protein folding. Under the first hypothesis, the Anfinsen cage hypothesis, the function of a molecular chaperonin is to provide a protected environment where folding of the protein to its native state can proceed without interference by pro-aggregation conditions in the cell (Martin, et al., *Nature* 352:36–42 (1991); Ellis, R. J., *Current Biology* 4:633–635 (1994)). Under the second hypothesis, the "iterative annealing" hypothesis, the function of the chaperonin is to partly unfold misfolded proteins (that is, kinetically trapped intermediates) with some of the energy of ATP hydrolysis being channeled into the conformational energy of the substrate polypeptide, forcing the polypeptide into a higher energy state from which it could once again attempt to refold correctly after being released into solution (Todd, M. J. et al., *Science* 265:659–666 (1994); Jackson, et al., *Biochemistry* 32:2554–2563 (1993); Weissman, et al., *Cell* 78:693–702 (1994); Weissman, J. S., & Kim, P. S., *Science* 253:1386–1393 (1991)).

The in vivo results discussed above are in many ways consistent with the more recent experiences with in vitro refolding of recombinant heterologous proteins expressed in *E. coli*. That is, while the primary amino acid sequence of a protein may contain sufficient information to determine its native folded conformation (Anfinsen, C. B., *Science* 181: 223–230 (1973)), the biochemical conditions in which the folding reaction takes place can strongly influence the partitioning between unfolded, aggregated, and correctly folded forms.

For example, pH can be understood to influence the folding reaction by its effect on the long range electrostatic interactions summed in the fourth term of the equation (4).

$$\Delta G_{fold} = \Delta G_{conf} + \Sigma \Delta g_{i,int} + \Sigma \Delta g_{i,s} + \Delta W_{el} + (\Delta G_{bind}) \quad \text{(Equation 4)}$$

where $\Delta G_{conf}$=conformational free energy (order/disorder term);

$\Delta g_{i,int}$=short range interactions (H-bonds, van der Walls interactions, salt bridges, cofactor binding, etc.);

$\Delta g_{i,s}$=short range interactions with solvent (hydrophobic effect, hydration of ions, etc.);

$\Delta W_{el}$=long range electrostatic interactions; and $\Delta G_{bind}$=ligand binding free energy As the pH of a protein solution is lowered below the pI for the protein, functional groups on the polypeptide become increasingly protonated, to the point where the electrostatic repulsion between protonated functional groups eventually out balances the other terms in the free energy equation (equation (4)), and the protein is no longer able to adopt the native conformation.

Another important biochemical parameter for protein folding is the solvent, water, which repels aliphatic and aromatic side chains (and possibly the main chain to some extent) to minimize their exposed surface area. The influence of solvent over the folding reaction is summed in the third term of the free energy equation (equation (4)). Certain salts are known to increase the hydrophobic interaction among protein side chains in water solutions. The effect depends upon the nature of the ions following the Hofmeister series: Cations: $Mg^{2+}>Li^+>Na+>K^+>NH_4^+$. Anions: $SO_4^{2-}>HPO_4^{2-}>$acetate>citrate>tartrate>$Cl^->NO_3^->ClO_3^->I^->ClO_4^->SCN^-$. Stabilizing Hofmeister anions, such as $SO_4^{2-}$ and $HPO_4^{2-}$ at 0.4 M have been found to increase the yield of correctly folded proteins (Creighton, T. E., In: *Proteins: Structures and Molecular Properties*, Freeman, N.Y., (1984)). This favorable outcome for the native conformation of the protein has been attributed to the cations' and anions' "salting out" effect which leads to the preferential hydration of the protein (Creighton, T. E., In: *Proteins: Structures and Molecular Properties*, Freeman, N.Y., (1984)).

Glycerol alters the solvation properties of water to favor the native conformation of proteins. The mechanism by which this occurs is the co-solvent exclusion and preferential hydration of the protein, not unlike the effect of salts of the Hofmeister series (Timasheff & Arakawa, In: *Protein Structure, A Practical Approach*, T. E. Creighton, ed., IRL Press, Oxford, UK (1989), pp. 331–354).

Another example of how the environment influences protein folding is the effect that known ligands and cofactors have on the yield of folded protein. Ligand binding has the effect of shifting the equilibrium from an unfolded state to a native-ligand complex through a coupling of the binding free energy to that of the folding reaction. The role of metal ions in the refolding of bovine carbonic anhydrase II has been described (Bergenhem & Carlsson, *Biochim. Biophys. Acta* 998:277–285 (1989)). Other biochemical parameters that have been shown to affect protein folding are: protein concentration, temperature, glutathione redox buffers (GSH, GSSG), the presence of detergents, and the presence of other additives, such as glycerol, arginine-HCl, polyethylene glycol (PEG), and organic solvents.

During incubation under refolding conditions, recombinant proteins can be immobilized to solid phase support. This configuration resembles the "Anfinsen cage" hypothesis for the function of GroEL and GroES where an unfolded protein becomes temporarily immobilized in a protected environment where folding to the native state can proceed without interference from competing aggregation reactions. Confirmation of protein folding on solid supports has now come from two recent reports in the literature. A polyhistidine tagged TIMP-2 protein could be refolded by dialysis while still bound to a metal chelate column (Negro, A. et al., *FEBS Lett.* 360:52–56 (1995)). A polyionic fusion peptide attached to the amino or carboxyl terminus of α-glucosidase allowed folding while bound to heparin-Sepharose resin at about 5 mg/mL (Rudolph & Lilie, *FASEB J.* 10:49–56 (1995)). A polyionic arginine tag methodology for immobilizing and refolding α-glucosidase is disclosed in Stempfer, G. et al., *Nature Biotechnology* 14:329–334 (1996).

In the present invention, the thermal shift assay is used to rank the efficacy of various refolding or renaturing conditions. Each of a multiplicity of aliquots of a protein of interest, which has been incubated under a variety of different biochemical folding conditions, are placed in a container in a multicontainer carrier. An aliquot of the native, fully functional protein of known concentration is placed in the control container. The samples can be placed in any multicontainer carrier. Preferably, each sample can be placed in a well of a multiwell microplate.

In considering the many biochemical variables that can influence the outcome of the protein folding reaction, optimization of protein folding is a multi-variable optimization problem, not unlike protein crystallization and quantitative structure activity relationships (QSAR) in drug discovery. Multi-variable optimization problems require large numbers of parallel experiments to collect as much data as possible in order to influence a favorable response. In this regard, both protein crystallization and QSAR analyses have greatly benefited from mass screening protocols that employ matrix arrays of incremental changes in biochemical or chemical composition.

The present invention can be used to rank the efficacies of refolding or renaturing conditions. Such conditions include, but are not limited to, the concentration of glycerol, the concentration of protein, the use of agents which catalyze the formation of disulfide bond formation, temperature, pH, ionic strength, type of solvent, the use of thiols such as reduced glutathione (GSH) and oxidized glutathione (GSSG), chaotropes such as urea, guanidinium chlorides, alkyl-urea, organic solvents such as carbonic acid amides, L-arginine HCl, Tris buffer, polyethylene glycol, nonionic detergents, ionic detergents, zwitterionic detergents, mixed micelles, and a detergent in combination with cyclodextrin. The present invention can be used regardless of whether a denaturation agent is removed from the protein using dialysis, column chromatographic techniques, or suction filtration.

Using a fluorescence thermal shift assay, the conditions which facilitate optimal protein refolding can be determined rapidly. In this embodiment, the renatured protein samples and a control protein sample (i.e., a sample of native protein in its fully functional form) are heated over a temperature range. At discrete temperature intervals, a fluorescence reading is taken. Alternatively, fluorescence readings can be taken during a continuous, pre-determined temperature profile. Thermal unfolding information (for example, thermal unfolding $T_m$) is generated for each sample. The $T_m$ for the native, fully functional reference protein is determined. The relative efficacies of the refolding conditions are ranked according to the magnitude of the fluorescence associated with unfolding at the $T_m$, of the native, fully functional reference protein, relative to the magnitude of the fluorescence of a known quantity of the sample proteins in the biochemical conditions at that $T_m$. The magnitude of fluorescence intensity change is used to monitor protein unfolding (reflected on the ordinate, or y-axis, of a thermal unfolding curve) is proportional to the amount of correctly folded protein.

The present invention provides a method for screening biochemical conditions that facilitate and optimize protein folding. To screen conditions for a given protein, it is first necessary to determine the thermal unfolding profile for a protein of interest. This is accomplished by generating thermal unfolding information using the microplate thermal shift assay. Various conditions can be optimized, including pH optimum, ionic strength dependence, concentration of salts of the Hofmeister series, glycerol concentration, sucrose concentration, arginine concentration, dithiothreitol concentration, metal ion concentration, etc.

Using the microplate thermal shift assay, one can determine one or more biochemical conditions have an additive effect on protein stability. Once a set of biochemical conditions that facilitate an increase in protein stability have been identified using the thermal shift assay, the same set of conditions can be used in protein folding experiments with recombinant protein. See FIG. 27. If the conditions that promote protein stability in the thermal shift assay correlate with conditions that promote folding of recombinant protein, conditions can be further optimized by performing additional thermal shift assays until a combination of stabilizing conditions that result in further increase protein stability are identified. Recombinant protein is then folded under those conditions. This process is repeated until optimal folding conditions are identified. Protein stability is expected to correlate with improved yields of protein folding. Yield of correctly folded protein can be determined using any suitable technique. For example, yield of correctly folded protein can be calculated by passing refolded protein over an affinity column, for example, a column to which a ligand of the protein is attached, and quantifying the amount of protein that is present in the sample. In this way, folding conditions can be assessed for their additive contributions to correct folding. The transition state for the protein folding reaction resembles the native form of the protein more than the denatured form. This has been demonstrated to be the case for may proteins (Fersht, A. R., *Curr. Op. Struct. Biol.* 7:3–9(1997)).

The methods of the present invention provide a rapid, high throughput approach to screening for combinations of biochemical conditions that favor the protein folding, using compounds of Formula I. The method does not require cumbersome and time consuming steps that conventional approaches to protein folding require. For example, using the method of the present invention, it is not necessary to dilute protein to large volumes and low protein concentrations (~10 µg/mL) in order to avoid aggregation problems associated with conventional methods of recombinant protein refolding. Suppression of protein aggregation will allow for screening biochemical parameters that shift the protein folding equilibrium (between the unfolded and the folded forms of proteins) to the correct native conformation.

Like protein stabilization, protein folding, ligand selection, and drug design, selection of conditions that promote protein crystallization is another multi-variable optimization problem that is solved using the methods and the apparatus of the present invention.

The methods of the present invention are also useful for determining conditions that facilitate protein crystallization. The crystallization of molecules from solution is a reversible equilibrium process, and the kinetic and thermodynamic parameters are a function of the chemical and physical properties of the solvent system and solute of interest (McPherson, A., In: *Preparation and Analysis of Protein Crystals*, Wiley Interscience (1982); Weber, P. C., *Adv. Protein Chem.* 41:1–36 (1991)) 1991). Under supersaturating conditions, the system is driven toward equilibrium where the solute is partitioned between the soluble and solid phase instead of the unfolded and native states. The molecules in the crystalline phase pack in ordered and periodic three dimensional arrays that are energetically dominated by many of the same types of cohesive forces that are important for protein folding, i.e., van der Waals interactions, electrostatic interactions, hydrogen bonds, and covalent bonds (Moore, W. J., in *Physical Chemistry*, 4th Ed., Prentice Hall, (1972), pp. 865–898).

Thus, in many ways protein crystallization can be viewed as a higher level variation of protein folding where whole molecules are packed to maximize cohesive energies instead of individual amino acid residues. Moreover, for both protein crystallization and protein folding, the composition of the solvent can make very important contributions to the extent of partitioning between the soluble (unfolded) and crystalline (native) forms. The cohesive interactions present in protein macromolecules and the role played by solvent in modulating these interactions for both protein folding and protein crystallization are complex and not fully understood at the present time. In this regard, biochemical conditions that promote protein stabililty and protein folding also promote protein crystallization.

For example, biochemical conditions that were found to increase the stability of D(II) FGF receptor 1 correlate with the conditions that facilitated the crystallization of x-ray diffraction quality protein crystals. Conditions that were employed to obtain crystals of D(II) FGFR1 protein are shown in Table 1.

Protein crystals were obtained in the pH range 7.4 to 9.2 in the presence of the Hofmeister salt $Li_2SO_4$ (65 to 72%). These crystallization conditions correlated with the pH optimum of about 8.0. Other salts of the Hofmeister series such as $Na_2SO_4$, $(NH_4)_2SO_4$ and $Mg_2SO_4$ were also found useful as additives for lowering the amount of $Li_2SO_4$ required as the precipitant. Clearly, these conditions for successful D(II) FGFR1 crystallization correlate closely with the stabilizing conditions that were identified using the microplate thermal shift assay.

Conditions that were identified as facilitating human α-thrombin stabilization also facilitate human α-thrombin protein crystallization. Conditions identified by three different investigators that facilitate crystallization of x-ray diffraction quality human α-thrombin crystals can be found in the following references: 1) Bode, W., et al., *Protein Sci.* 1:426–471 (1992); 2) Vijayalakshmi, J. et al., *Protein Sci.* 3:2254–22271 (1994); and 3) Zdanov, A. et al., *Proteins. Struct. Funct. Genet.* 17:252–265 (1993)).

The conditions summarized in Table 2 correlate closely with the conditions identified in the microplate thermal shift assay as facilitating human α-thrombin stability. Crystals formed near a pH optimum of about 7.0. Furthermore, there is a clear preference for the presence of 0.1 to 0.5 M NaCl (50% of the conditions) or 0.1 to 0.2 M $NaHPO_4$. This is consistent with the recently discovered $Na^+$ binding site (Dang et al., *Nature Biotechnology* 15:146–149 (1997)) and microplate thermal shift assay results in FIGS. 17A–D and 18. All of the human α-thrombin samples described in Table 2 that have yielded good crystals are complexed with a ligand, thereby further stabilizing the native structure of this protein beyond that acquired from the biochemical conditions.

TABLE 1

D(II) FGFR1 Crystallization Conditions

| Buffer | Precipitant | Additive | Protein Concentration |
| --- | --- | --- | --- |
| 50 mM Hepes pH 7.4 | 72% $Li_2SO_4$ | | 10 mg/ml (10 mM Hepes pH 7.5) |
| 50 mM Hepes pH 7.4 | 72% $Li_2SO_4$ | 3.4 mM $ZnSO_4$ | 10 mg/ml (10 mM Hepes pH 7.5) |
| 50 mM Hepes pH 7.4 | 68% $Li_2SO_4$ | 1% PEG 8000 | 10 mg/ml (10 mM Hepes pH 7.5) |
| 50 mM Hepes pH 7.4 | 66% $Li_2SO_4$ | 3.4 mM $Na_2SO_4$ | 10 mg/ml (10 mM Hepes pH 7.5) |
| 50 mM Hepes pH 7.4 | 66% $Li_2SO_4$ | 5.3 mM $(NH_4)_2SO_4$ | 10 mg/ml (10 mM Hepes pH 7.5) |
| 50 mM Hepes pH 7.4 | 66% $Li_2SO_4$ | 2.1 mM $MgSO_4$ | 10 mg/ml (10 mM Hepes pH 7.5) |
| 10 mM Tris Hcl, pH 8.0 | 65% $Li_2SO_4$ | | 10 mg/ml (10 mM Hepes pH 7.5) |
| 20 mM glycine, pH 5.2 | 68% $Li_2SO_4$ | | 10 mg/ml (10 mM Hepes pH 7.5) |

Protein crystallization is a slow and tedious process that has historically been the rate determining step for the X-ray diffraction determination of protein and nucleic acid structures. The method and apparatus of the present invention facilitate the rapid, high-throughput elucidation of conditions that promote the stability of a given protein and thus the formation of X-ray quality protein crystals.

When a protein is more stable, it has fewer thermodynamic motions that inhibit packing into a crystal lattice. With fewer motions, the protein fits better into a crystal lattice. Using conventional crystallization methods, crystallization experiments are set up at room temperature for weeks at a time. Over time, protein unfolding occurs. Using the methods of the present invention, conditions that stabilize a protein are examined over a temperature range.

Optimization of protein stability, ligand binding, protein folding, and protein crystallization are multi-variable events. Multi-variable optimization problems require large numbers of parallel experiments to collect as much data as possible in order to determine which variables influence a favorable response. For example, multi-variable optimization problems require large numbers of parallel experiments to collect as much data as possible in order to determine which variables influence protein stabililty. In this regard, both protein crystallization and quantitative structure-activity relationship analyses have greatly benefited from mass screening protocols that employ matrix arrays of incremental changes in biochemical or chemical composition. Thus, in much the same way that quantitative structure-activity relationships are constructed to relate variations of chemical functional groups on ligands to their effect on binding affinity to a given therapeutic receptor, the methods and apparatus of the present invention facilitate the construction of a quantitative model that relates different biochemical conditions to experimentally measured protein stability, ligand specificity, folded protein yield, and crystallized protein yield.

Using the fluorescence microplate thermal shift assay, one can determine one or more biochemical conditions that have an additive effect on protein stability. Once a set of biochemical conditions that facilitate an increase in protein stability have been identified using the thermal shift assay, the same set of conditions can be used in protein folding experiments with recombinant protein. If the conditions that promote protein stability in the thermal shift assay correlate with conditions that promote folding of recombinant protein, conditions can be further optimized by performing additional thermal shift assays until a combination of stabilizing conditions that result in further increase protein stability are identified. Recombinant protein is then folded under those conditions. This process is repeated until optimal folding conditions are identified.

The present invention offers a number of advantages over previous technologies that are employed to optimize multi-variable events such as protein stabilization, ligand binding, protein folding, and protein crystallization. Foremost among these advantages is that the present invention facilitates high throughput screening. The use of a compound of Formula I to practice the microplate thermal shift assay affords increased assay sensitivity and increased assay throughput, because these dyes have long emission wavelengths, high extinction coefficients, high quantum yields, and large Stokes shifts.

Further, the methods of the present invention offer a number of advantages over previous technologies that are employed to screen combinatorial libraries. Foremost among these advantages is that the present invention facilitates high throughput screening of combinatorial libraries for lead compounds. Many current library screening technologies simply indicate whether a ligand binds to a receptor or not. In that case, no quantitative information is provided. No information about the relative binding affinities of a series of ligands is provided. In contrast, the present invention facilitates the ranking of a series of compounds for their relative affinities for a target receptor. With this information in hand, a structure-activity relationship can be developed for a set of compounds. The ease, reproducibility, and speed of using ligand-dependent changes in midpoint unfolding temperature ($T_m$) to rank relative binding affinities makes the present invention a powerful tool in the drug discovery process.

Typically, the conventional kinetic screening approach requires at least six additional well assays at six different concentrations of inhibitor to determine a $K_i$. Using the present invention, throughput is enhanced by about 6 fold with compounds of Formula I over the enzyme-based assays because one complete binding experiment can be performed in each well of a multiwell microplate. The kinetic screening approaches are even further limited by the usual compromise between dilution and signal detection, which usually occurs at a protein concentration of about 1 nM. In this regard, the calorimetric approaches, either differential scanning calorimetry or isothermal titrating calorimetry, are at an even worse disadvantage since calorimetric approaches are limited to solitary binding experiments, usually one per hour. In contrast, the present invention affords a wide dynamic range of measurable binding affinities, from ~$10^{-4}$ to $10^{-15}$ M, in a single well.

A very important advantage of the present invention is that it can be applied universally to any receptor that is a drug target. Thus, it is not necessary to invent a new assay every time a new receptor becomes available for testing. When the receptor under study is an enzyme, researchers can determine the rank order of affinity of a series of compounds more quickly and more easily than they can using conventional kinetic methods. In addition, researchers can detect ligand binding to an enzyme, regardless of whether binding occurs at the active site, at an allosteric cofactor binding site, or at a receptor subunit interface. The present invention is equally applicable to non-enzyme receptors, such as proteins and nucleic acids.

In another emodiment of the present invention, certain compounds according to Formula I can be used as reactive probes. Said reactive probes include amine reative probes, thiol reactive probes, hydroxy reactive probes, aldehyde reactive probes, ketone reactive probes, and carboxylic acid reactive probes.

Certain compounds of Formula I are useful as amine reactive probes. Amine reactive probes are compounds of Formula I that react with a substance of interest that contains a free amine moiety. The amine reactive probe contains one or more amine reactive moieties. A free amine moiety is a —$NH_2$, —$NHR^a$, —$NR^aR^b$, or $NR^aR^bR^c$, wherein $R^a$, $R^b$, and $R^c$ are, independently from one another, hydrogen, alkyl, or, together with the nitrogen to which they are bound, form a saturated or unsaturated ring. The amine reactive probe may react with a free amine group on the substance of interest to form a covalent or ionic conjugate. Preferably, the amine reactive probe reacts with the free amine group on the substance of interest to form a covalent conjugate. An amine reactive moiety is a carboxyl acid, carboxylic ester, acetyl azide, alkyl halide, aryl halide, dichlorotriazene, isothiocyanate, sulfonyl halide, sulfosuccinimidyl ester, acyl halide, or aldehyde. Amine reactive probes have a number of uses, including determination of the presence of amines on a substance; immunohistochemistry; in situ hybridization; neuronal tracing; oligonucleotide labeling; and automated DNA sequencing applications.

Certain compounds of Formula I are useful as thiol reactive probes. Thiol reactive probes are compounds of Formula I that react with a substance of interest that contains a free thiol group. The thiol reactive probe contains one or more thiol reactive moieties. A free thiol group moiety is SH. The thiol reactive probe may react with a free thiol moiety on the substance of interest to form a covalent or ionic conjugate. Preferably, the thiol reactive probe reacts with the free thiol moiety to form a covalent conjugate. A thiol reactive moiety is an isothiocyanate, succinimidyl ester, iodoacetamide, maleimide, aziridine, disulfide, alkyl halide, acrylate, or α-halo ketone. Thiol reactive probes are useful for producing protein conjugates, derivatizing low molecular weight thiol compounds, using in analytical assays. For example, see Shimada et al. *J Chromat. B. Biomed. Appl.* 659:227–241 (1994).

Certain compounds of Formula I are useful as hydroxy reactive probes. Hydroxy reactive probes are compounds of Formula I that react with a substance of interest that contains a free hydroxy moiety. The hydroxy reactive probe contains one or more hydroxy reactive moieties. A free hydroxy moiety is a —OH. The hydroxy reactive probe may react with a free hydroxy group on the substance of interest to form a covalent or ionic conjugate. Preferably, the hydroxy reactive probe reacts with a free hydroxy group on the substance of interest to form a covalent conjugate. A hydroxy reactive moiety is a carboxylic acid, carboxylic ester, sulfonyl halide, sulfonyl chloride, haloacetamide, isocyanate, isothiocyanate, boronic acid, acyl nitrile, acid halide, acid chloride, acyl azide, triarylalkylhalides. Hydroxy reactive probes have a number of uses, including determination of the presence of hydroxyls on a substance; immunohistochemistry; in situ hybridization; neuronal tracing; determination of the number of hydroxy groups on a substance (e.g., Yan et al., *Anal. Chem.* 71:4564 (1999)).

Certain compounds of Formula I are useful as aldehyde reactive probes. Aldehyde reactive probes are compounds of Formula I that react with a substance of interest that contains a free aldehyde moiety. The aldehyde reactive probe contains one or more aldehyde reactive moieties. A free aldehyde moiety is a —C(O)H. The aldehyde reactive probe may react with a free aldehyde group on the substance of interest to form a covalent or ionic conjugate. Preferably, the aldehyde reactive probe reacts with a free aldehyde group on the substance of interest to form a covalent conjugate. An aldehyde reactive moiety is a primary or secondary amine, which may be aliphatic or aromatic, a hydrazide, a semicarbazide, or a carbohydrazide. Aldehyde reactive probes have a number of uses, including determination of the presence of aldehyde groups on a substance; immunohistochemistry; in situ hybridization; neuronal tracing; analysis of compounds by capillary electrophoresis; sequencing of carbohydrate polymers; and staining lipopolysaccharides.

Certain compounds of Formula I are useful as ketone reactive probes. Ketone reactive probes are compounds of Formula I that react with a substance of interest that contains a free ketone moiety. The ketone reactive probe contains one or more ketone reactive moieties. A free ketone moiety is a —C(O)—. The ketone reactive probe may react with a free ketone group on the substance of interest to form a covalent or ionic conjugate. Preferably, the ketone reactive probe reacts with a free ketone group on the substance of interest to form a covalent conjugate. A ketone reactive moiety is a primary or secondary amine, which may be aliphatic or aromatic, a hydrazide, a semicarbazide, or a carbohydrazide. Ketone reactive probes have a number of uses, including determination of the presence of ketone groups on a substance; immunohistochemistry; in situ hybridization; neuronal tracing; analysis of compounds by capillary electrophoresis; sequencing of carbohydrate polymers; and staining lipopolysaccharides.

Certain compounds of Formula I are useful as carboxylic acid reactive probes. A carboxylic reactive probe is fluorescent probe that reacts with a substance that contains a free carboxylic moiety. The carboxylic acid reactive probe contains one or more carboxylic acid reactive moieties. A free carboxylic acid moiety is a —$CO_2H$. The carboxylic acid reactive probe may react with a carboxylic acid group on the substance of interest to form a covalent or ionic conjugate. Preferably, the carboxylic acid reactive probe reacts with the free carboxylic acid group on the substance of interest to form a covalent conjugate. A carboxylic acid reactive moiety is an amine, hydroxy, carboxylic acid, sulfonyl halide, haloacetamide, isocyanate, isothiocyanate, acyl nitrile, acid halide, acid chloride, acyl azide, triarylalkylhalide, amine, hydrazine. When the carboxylic acid reactive moiety is an amine, prerably an amide conjugate will be formed. When the carboxylic acid reactive moiety is a hydroxy, preferably an ester conjugate will be formed. Carboxylic acid reactive probes have a number of uses, including determination of the presence of carboxylic acid groups on a substance; immunohistochemistry; in situ hybridization; neuronal tracing; oligonucleotide labeling; and automated DNA sequencing applications.

When using a compound according to Formula I as an amine reative probes, a thiol reactive probe, a hydroxy reactive probe, an aldehyde reactive probes, a ketone reactive probe, or a carboxylic acid reactive probe, it may be advantageous to use one or more additional chemical reagents to facilitate the reaction between the probe compound and the substance of interest. Such compounds include dicyclohexylcarbodiimide (DCC), diethylazodicarboxylate (DEAD), diisopropylazodicarboxylate (DIAD), N-hydroxysuccinimide (NHS), and EDAC.

If the target molecule or receptor to be studied is a nucleic acid, fluorescence spectrometry can be performed using fluorescence resonance emission transfer. The transfer of fluorescent energy, from a donor fluorophore on one strand of an oligonucleotide to an acceptor fluorophore on the other strand, is monitored by measuring the fluorescence of the acceptor fluorophore. Unfolding or denaturation prevent the transfer of fluorescent energy. The fluorescence resonance emission transfer methodology is well known to those skilled in the art. For example, see Ozaki, H., et al., *Nucleic Acids Res.* 20:5205–5214 (1992); Clegg, R. M., et al., *Proc. Natl. Acad. Sci. USA* 90:2994–2998 (1993); Clegg, R. M., et al., *Biochemistry* 31:4846–4856 (1993).

One strand of a double-stranded oligonucleotide will contain the donor fluorophore. The other strand of the oligonucleotide will contain the acceptor fluorophore. For a nucleic acid to "contain" a donor or an acceptor fluorophore, the fluorophore can be incorporated directly into the oligonucleotide sequence. Alternatively, the fluorophore can be attached to either the 5'- or 3'-terminus of the oligonucleotide.

Compounds of Formula I are useful in fluorescence resonance energy transfer studies of nucleic acids, including oligonucleotides and polynucleotides. In particular, the compounds of the present invention can be used to determine the structure and conformational transitions of nucleic acids. For example, see Clegg, et al., *Proc. Natl. Acad. Sci. USA* 90:2994–2998 (1993).

A donor fluorophore is one which, when excited by light, will emit fluorescent energy. The energy emitted by the donor fluorophore is absorbed by the acceptor fluorophore. The term "donor fluorophore" encompasses all fluorophores including, but not limited to, carboxyfluorescein, iodoacetamidofluorescein, and fluorescein isothiocyanate. The term "acceptor fluorophore" encompasses all fluorophores including, but not limited to, iodoacetamidoeosin and tetramethylrhodamine.

Compounds of Formula I are useful as molecular beacons, as described in U.S. Pat. No. 6,037,130, which is hereby fully incorporated by reference.

Compounds of Formula I are useful in monitoring the sequence and mechanisms of action of various cellular processes and signal pathways. The time course, nature, and sequence of the different cellular processes can be elucidated by in situ observation using the compounds of Formula I. Specific inhibitors and/or activators of the cellular processes and signal pathways being studied may optionally be used in addition to compounds of Formula I. For example, the onset and progression of the acrosomal reaction, can be monitored using compounds of Formula I. (For example, see Rockwell, et al. *Mol. Reprod. Dev.* 55(3):335–339 (2000)). When using compounds of Formula I to monitor the acrosomal reaction, other agents and compounds may be administered to the test conditions. In this way, it is possible to screen for compounds and agents that inhibit the acrosomal reaction.

Compounds of Formula I are also useful for monitoring and visualizing the endoplasmic reticulum (ER) in cells. The compounds of the present invention may be administered to cells so that the ER can be visualized. For example, see Skepper, et al., *J. Physiol.* 527P:72P (2000). See also R. Haugland, *Molecular Probes Handbook of Fluorescent Probes and Research Chemicals*, Chapters 1–3 (1996). Other agents may be used in addition to the compounds of Formula I. In this way, the effects of other agents and compounds on the ER may be visualized. Additional compounds that can be used include nocodazole, colchicines, and TAXOL. Changes in the distribution of the dye within the cell after administration of other agents and compounds provides information regarding the action of said agents and compounds.

Certain compounds of Formula I are useful in monitoring and visualizing organelles that comprise an acidic environment. The compounds of the present invention typically concentrate within organelles that have an acidic interior. Typically, acidic organelles are organelles in which the pH of its interior is less than 7, preferably less than 6. Such organelles include lysosomes.

Compounds of Formula I are also useful detecting the concentration of zinc ions. In particular, the compounds of the present invention are useful for quantitating free $Zn^{2+}$ to levels as low as picomolar concentrations. For example, see Thompson et al. *J. Biomed. Opt.* 5(1):17–22 (2000). Compounds of Formula I, when used in conjunction with apocarbonic anhydrase enzymes, can be used to measure the level of free zinc with high selectivity.

In all methods of using a compound according to Formula I, the concentration of said compound is from about 0.1 nM to about 10,000 μM. Other preferred concentrations include from about 1 nM to about 1,000 μM, from about 0.1 μM to about 500 μM, from about 1 μM to about 500 μM, and from about 1 μM to about 100 μM.

Preparation of Compounds

The present invention is also directed to the multi-step synthesis of compounds of Formula I, including intermediates and intermediate reaction steps as herein described.

Scheme I: The compounds of Formula I can be prepared according to the reaction as shown in Scheme I, wherein $R^1$, $R^2$, and A are defined as above. 2-(4'-Chlorosulfonylphenyl)-5-(4''-dimethylaminophenyl)oxazole (2, DAPOXYL sulfonyl chloride) is stirred with an appropriate amine (3) in a suitable solvent to form a compound of Formula I (1). Compound 2 can be prepared according to Scheme II and as detailed in Diwu et al. *Photochem. Photobiol.* 66(4):424–431 (1997).

Scheme I

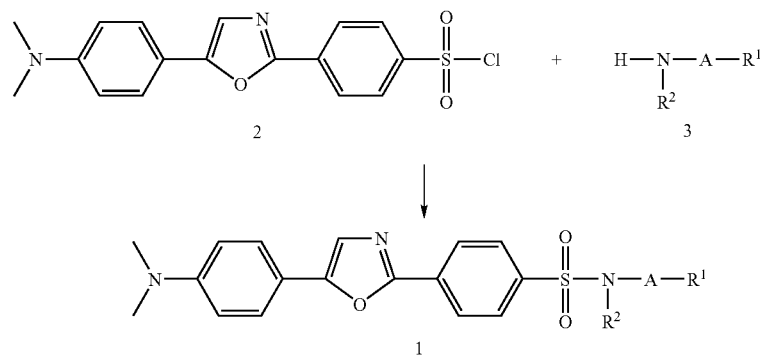

Scheme II

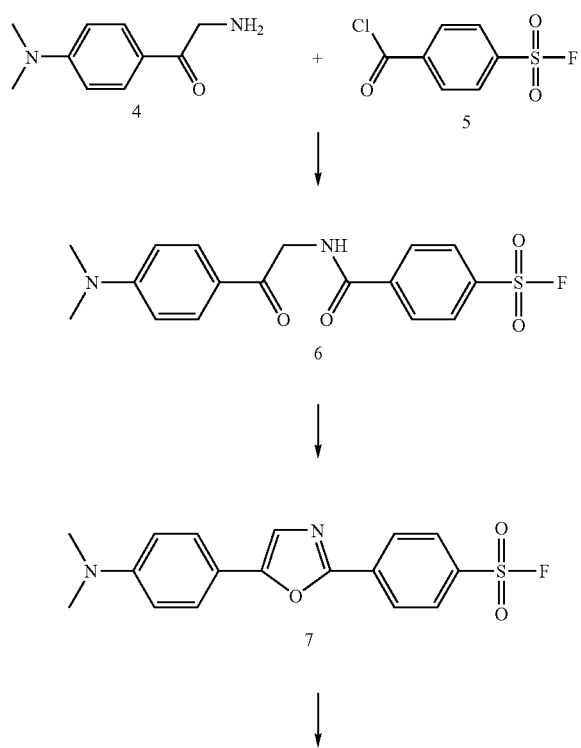

Scheme II: 2-(4'-Fluorosulfonylbenzoylamino)-4"-dimethyl-aminoacetophenone is prepared by reacting (6) by reacting 2-amino-4'-dimethylaminoacetophenone (4) with 4-fluorosulfonylbenzoyl chloride (5) in a solvent, such as dichloromethane, chloroform, or toluene. Compound 6 is dehydrated, e.g., by using concentrated sulfuric acid, to yield 2-(4'-fluorosulfonylphenyl)-5-(4"-dimethylaminophenyl)oxazole (7, DAPOXYL sulfonyl fluoride). Compound 7 is then reacted with base, e.g., 10% NaOH, to yield 2-(4'-sulfophenyl)-5-(4"-dimethylaminophenyl)oxazole, sodium salt (8, DAPOXYL sulfonic acid, sodium salt). Compound 8 is reacted with a suitable chlorinating agent, e.g., POCl$_3$, PCl$_5$, or SOCl$_2$, to provide 2-(4'-chlorosulfonylphenyl)-5-(4"-dimethylaminophenyl)oxazole (2, DAPOXYL sulfonyl chloride).

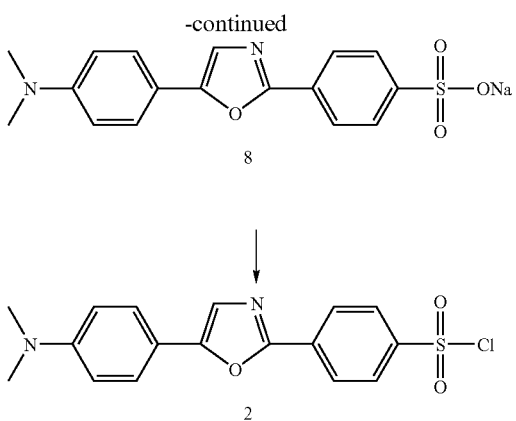

The amine (3) used in Scheme I can be any suitable mean that produces a compound according to Formula I. The amines used in Scheme I may be prepared according to well known methods in the art. Additional compounds according to Formula I are made by reacting 2-(4'-chlorosulfonylphenyl)-5-(4"-dimethylaminophenyl)oxazole (2, DAPOXYL sulfonyl chloride) with any one of the following amines: (cyclopropylmethyl)amine; 2-(cyclopropyl)ethylamine; 3-(cyclobutyl)-1-propylamine; N-methyl-3-cyclopentyl-1-pentylamine; 4-cyclohexyl-1-pentylamine; 4-cyclohexyl-2-pentylamine; cyclopropylamine; cyclobutylamine; cyclopentylamine; N-methylcyclopentylamine; cyclohexylamine; N-hexylcyclohexylamine; cycloheptylamine; cyclooctylamine; cyclononylamine; cyclodecylamine; 2-methylcyclopropylamine; 2-methoxycyclopentylamine; 3-hydroxycyclopentylamine; 3-(methoxycarbonyl)cyclopentylamine; 2-(hydroxymethyl)cyclopentylamine; 1,4-cyclohexyldiamine; N,N-dimethyl-1,4-cyclohexyldiamine; 4-oxo-2-cyclohexylamine; 1,2-diaminocyclohexane; 1-amino-cis-cyclopentane-1,3-dicarboxylic acid; cis-1-amino-2-indanol; [2-(benzylamino)cyclohexyl]methanol; 1-amino-2-phenylcyclopropanecarboxylic acid; cyclopropenylamine; cyclobutenylamine; cyclopentenylamine; N-ethylcyclopentenylamine; cyclohexenylamine; N-benzylcyclohexenylamine; cycloheptenylamine; cyclooctenylamine; cyclononenylamine; cyclodecenylamine; 2-methyl-3-cyclopropenylamine; 4-methoxy-2-cyclopentenylamine; 3-hydroxy-2-cyclopentenylamine; 5-(methoxycarbonyl)-2- cyclopentylamine; 4-(hydroxymethyl)-3-cyclopentylamine; 4-oxo-2-cyclohexenylamine; 4-amino-2-cyclopentene-1-carboxylic acid; N-ethyl-2-(2-hydroxycyclopropyl)ethylamine; 3-(3-carboxycyclobutyl)-1-propylamine; N-methyl-3-(3-(dimethylamino)cyclopentyl)-1-pentylamine; 4-(2-chlorocyclohexyl)-1-pentylamine; 4-(3-ethoxycyclohexyl)-2-pentylamine; isopinocampheylamine; 3-pinanemethylamine; and myrtanylamine.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: tromethamine; 2,3-dihydroxy-1-propylamine; 1,2-dihydroxy-2-propylamine; 2,4-dihydroxy-1-butlylamine; 3-hydroxy-2-hexylamine; 3-hydroxymethyl-2-hexylamine; 6-hydroxy-1-hexylamine; 2-amino-1,2-diphenylethanol; N-ethyl-6-hydroxy-2-(methoxycarbonyl)methylhexylamine; 4-hydroxy-2-butenyl-1-amine; N-methyl-4-hydroxy-2-butenyl-1-amine; 5-hydroxy-3-pentenyl-2-amine; 4-hydroxy-2-butynyl-1-amine; N-methyl-4-hydroxy-2-butynyl-1-amine; 5-hydroxy-3-pentynyl-2-amine; 2-amino-2-deoxy-glucose;

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: 2-aminoacetic acid; 4-aminobutyric acid; 6-aminohexanoic acid; 7-aminoheptanoic acid; N-benzyl-4-aminobutyric acid; N-propyl-6-aminohexanoic acid; N-isobutyl-7-aminoheptanoic acid; 4-amino-2-hydroxy-butyric acid; 6-amino-3-methoxy-hexanoic acid; 7-amino-2-(4-aminophenyl)heptanoic acid; N-benzyl-4-aminobutyric acid; N-propyl-6-amino-4-isopropylhexanoic acid; N-isobutyl-7-amino-3-chloroheptanoic acid; 4-aminobutenoic acid; 6-aminohexenoic acid; 7-aminoheptenoic acid; N-benzyl-4-aminobutenoic acid; N-propyl-6-aminohexenoic acid; N-isobutyl-7-aminoheptenoic acid; 4-amino-2-hydroxy-butenoic acid; 6-amino-3-methoxyhexenoic acid; 7-amino-2-(4-aminophenyl)heptenoic acid; N-benzyl-4-aminobutenoic acid; N-propyl-6-amino-4-isopropylhexenoic acid; N-isobutyl-7-amino-3-chloroheptenoic acid; 4-aminobutynoic acid; 6-aminohexynoic acid; 7-aminoheptynoic acid; N-benzyl-4-aminobutynoic acid; N-propyl-6-aminohexynoic acid; N-isobutyl-7-aminoheptynoic acid; 4-amino-2-hydroxy-butynoic acid; 6-amino-2-methoxyhexynoic acid; 7-amino-2-(4-aminophenyl)heptynoic acid; N-benzyl-4-aminobutynoic acid; N-propyl-6-amino-4-isopropylhexynoic acid; N-isobutyl-7-amino-3-chloroheptynoic acid; and esters thereof.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: 2-phenylethylamine; 3-phenyl-1-propylamine; 4-phenyl-1-butylamine; 3-phenyl-1-butylamine; 5-phenyl-1-pentylamine; 4-phenyl-1-pentylamine; 4-phenyl-2-pentylamine; 6-phenyl-1-hexylamine; 5-phenyl-1-hexylamine; 5-phenyl-2-hexylamine; 7-phenylheptylamine; 8-phenyloctylamine; N-benzyl-2-phenylethylamine; N-propenyl-3-phenyl-1-propylamine; N-benzyl-4-phenyl-1-butenylamine; N-ethyl-3-phenyl-1-butylamine; N-methyl-5-phenyl-1-pentylamine; N-cyclopropyl-4-phenyl-1-pentyl amine; N-butyl-4-phenyl-2-pentylamine; N-benzyl-6-phenyl-1-hexylamine; N-hexenyl-5-phenyl-1-hexylamine; N-n-butyl-5-phenyl-2-hexylamine; N-propynyl-7-phenylheptylamine; N-benzyl-8-phenyloctylamine; 3-phenyl-1-propenylamine; 4-phenyl-1-butenylamine; 3-phenyl-1-butenylamine; 5-phenyl-1-pentenylamine; 4-phenyl-1-pentenylamine; 4-phenyl-2-pentenylamine; 6-phenyl-1-hexenylamine; 5-phenyl-1-hexenylamine; 5-phenyl-2-hexenylamine; 7-phenylheptenylamine; 8-phenyloctenylamine; N-propenyl-3-phenyl-1-propenylamine; N-benzyl-4-phenyl-1-butenylamine; N-ethyl-3-phenyl-1-butenylamine; N-methyl-5-phenyl-1-pentenylamine; N-cyclopropyl-4-phenyl-1-pentenylamine; N-butyl-4-phenyl-2-pentenylamine; N-benzyl-6-phenyl-1-hexenylamine; N-hexenyl-5-phenyl-1-hexenylamine; N-n-butyl-5-phenyl-2-hexenylamine; N-propynyl-7-phenylheptenylamine; N-benzyl-8-phenyloctenylamine; 3-phenyl-1-propynylamine; 4-phenyl-1-butynylamine; 3-phenyl-1-butynylamine; 5-phenyl-1-pentynylamine; 4-phenyl-1-pentynylamine; 4-phenyl-2-pentynylamine; 6-phenyl-1-hexynylamine; 5-phenyl-1-hexynylamine; 5-phenyl-2-hexynylamine; 7-phenylheptynylamine; 8-phenyloctynylamine; N-propenyl-3-phenyl-1-propynylamine; N-benzyl-4-phenyl-1-butynylamine; N-ethyl-3-phenyl-1-butynylamine; N-methyl-5-phenyl-1-pentynylamine; N-cyclopropyl-4-phenyl-1-pentynylamine; N-butyl-4-phenyl-2-pentynylamine; N-benzyl-6-phenyl-1-hexynylamine; N-hexenyl-5-phenyl-1-hexynylamine; N-n-butyl-5-phenyl-2-hexynylamine; N-propynyl-7-phenylheptynylamine; N-benzyl-8-phenyloctynylamine; 2-hydroxymethyl-2-phenylethylamine; 2-methoxymethyl-3-phenyl-1-propylamine; 3-nitro-4-phenyl-1-butylamine; 2-dimethylamino-3-phenyl-1-butylamine; 5-(4-aminophenyl)-1-pentylamine; 4-(3,4-methylenedioxyphenyl)-1-pentylamine; 4-(3-carboxyphenyl)-2-pentylamine; 6-phenyl-3-oxo-1-hexylamine; 5-(4-phenoxyphenyl)-1-hexylamine; 5-phenyl-4-2-hexylamine; 7-(3-guanidinophenyl)-1-heptylamine; and 8-phenyl-3-(methysulfonyl)octylamine.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: N-benzyl-2-methylthio-2-phenylethylamine; N-propenyl-3'-(4-(phenylethyl)phenyl)-1-propylamine; N-benzyl-3-aminoethyl-4-phenyl-1-butylamine; N-ethyl-2-(2-(dimethylamino)ethoxy)$_3$-phenyl-1-butylamine; N-methyl-3-benzenesulfonyl-5-phenyl-1-pentylamine; N-cyclopropyl-3-butoxycarbonylamino-4-phenyl-1-pentylamine; N-butyl-4-(4-(aminomethyl)phenyl-2-pentylamine; N-benzyl-6-phenyl-1-hexylamine; N-hexenyl-5-phenyl-1-hexylamine; N-n-butyl-3,4-dihydroxy-5-phenyl-2-hexylamine; N-propynyl-3,4,5-trihydroxy-7-phenylheptylamine; N-benzyl-8-(2,4,6-trihydroxyphenyl)octylamine; 2-(4-bromo-2,5-dimethoxyphenyl)-1-ethylamine; 2,3-dichloro-α-methylbenzylamine; 2-amino-1-(4-nitrophenyl)-1,3-propanediol; 2-amino-1-phenyl-1,3-propanediol; 2-amino-3-methoxy-1-phenyl-1-propanol; bis(α-methylbenzyl)amine; N-(1-phenylethyl)-1-azabicyclo [2.2.2]octan-3-amine; 1,2-diphenylethylenediamine; 1-phenylethylenediamine; 1,3-diphenylpropylenediamine; 6-methylamino-4,4-diphenylheptan-3-one; 1-(1-naphthyl)ethylamine; 2-(1-naphthyl)ethylamine; 3-(1-naphthyl)propyl-1-amine; 4-(1-naphthyl)butyl-1-amine; 3-(1-naphthyl)butyl-1-amine; and 4-(1-naphthyl)butyl-1-amine.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: 2-(2-pyridyl)ethylamine; 3-(2-pyridyl)-1-propylamine; 4-(2-pyridyl)-1-butylamine; 2-(2-quinolinyl)ethylamine; 3-(2-imidazolyl)-1-propylamine; 4-(3-isoxazolyl)-1-butylamine; 5-(3-pyridyl)-1-pentylamine; 2-(6-amino-2-pyridyl)ethylamine; 3-(6-chloro-2-pyridyl)-1-propylamine; 4-(6-methoxy-3-pyridyl)-1-butylamine; 3-hydroxy-5-(3-pyridyl)-1-pentylamine; and α-amino-3-hydroxy-5-methylisoxazole-4-propionic acid.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: azetidine; azeridine; pyrollidine; piperidine; piperazine; azepine; 2-methoxycarbonylazetidine; azeridine; 3-(hydroxymethyl) pyrollidine; 4-(guanidino)piperidine; 2-carboxymethylpiperazine; and 3-ethylazepine.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: phosphoric acid monoaminoethyl ester; phosphoric acid mono-(3-aminopropyl)ester; phosphoric acid monoaminoethyl ester diethyl ester; phosphoric acid mono-(3-aminopropyl)ester diethyl ester; (1-aminopropyl)phosphonic acid; (1-amino-2-methylpropyl)phosphonic acid; (1-aminobutyl)phosphonic acid; (1-aminohexyl)phosphonic acid; (1-aminoethyl)phosphonic acid; (1-aminoethyl)phosphonic acid diisopropyl ester; (2-benzylaminoethyl)phosphinic acid monoethyl ester; (1-aminopropyl)phosphinic acid; (1-amino-2-methylpropyl) phosphinic acid; (1-aminobutyl)phosphinic acid; (1-aminohexyl)phosphinic acid; (1-aminoethyl)phosphinic acid; (1-aminoethyl)phosphinic acid diisopropyl ester; and (2-benzylaminoethyl)phosphinic acid monoethyl ester.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: aspartic acid; glycine; alanine; lysine; tryptophan; tyrosine; proline; phenylalanine; homophenylalanine; homotyrosine; valine; leucine; isoleucine; serine; cysteine; cystine; homoserine; methionine; asparagine; glutamine; arginine; histidine; threonine; thyroxine; liothyronine (O-(4-hydroxy-3-iodophenyl)-3,5-diiodo-L-thyroxine); hydroxyproline; ethyl 2-amino-4-cyclohexylbutyrate; 3-hydroxyphenylglycine; and α-methyl-4-carboxyphenylglycine.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: serotonin; epinephrine; norepinephrine; nornicotine; L-dopa; methyldopa; carbidopa; metyrosine; L-dihydroxyphenylserine; p-tyramine; dopamine; γ-aminobutryic acid; ephedrine; amphetamine; methamphetamine; mescaline; 1-(2,5-dimethoxy-4-methylphenyl)-2-aminopropane; p-methoxyamphetamine; 3,4-methylenedioxyamphetamine; 2,5-dimethoxy-4-bromoamphetamine; 3,4-methylenedioxy-N-ethylamphetamine; 6-hydroxy-3,4-methylenedioxymethamphetamine; 1-(2,5-dimethoxy-4-iodophenyl)-2-aminopropane; 3-(4-chlorophenyl)-γ-aminobutyric acid; isoproterenol; N-tert-butylnorepinephrine; terbutaline; albuterol; isoetharine; epinephryl borate; dipivefrin; metaproterenol; bitolterol; colterol; phenylpropanolamine; mephentermine; metaraminol (α-(1-aminoethyl)-m-hydroxybenzyl alcohol); hydroxyamphetamine (1-(4-hydroxyphenyl)-2-aminopropane); levonordefrin (α-(1-aminoethyl)-3,4-dihydroxybenzyl alcohol); ethylnorepinephrine; methoxyphenamine (2-(2-methoxyphenyl)isopropylmethylamine); methoxamine (2-amino-1-(2,5-dimethoxyphenyl)propanol); propanolol; dicholoroisoproterenol; 4-hydroxypropanolol; proactolol; metoprolol; nadolol; timolol; butoxamine; atenolol; acebutolol; diacetolol; pindolol; esmolol; and betaxolol.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: phenteramine; diethylpropion; fenfluramine; chlorphentermine; clortermine; phenmetrazine; methylphenidate; phenelzine (2-(phenylethyl)hydrazine); tranylcypromine (2-phenylcyclopropylamine); desipramine (10,11-dihydro-N-methyl-5H-dibenz[b,f]azepine-5-propanamine); nortriptyline (3-(10,1'-dihydro-5H-dibenzo[a,d]cyclohepten-5-ylidene)-N-methyl-1-propanamine); protriptyline (N-methyl-5H-dibenzo[a,d] cyclheptene-5-propylamine; maprotiline (N-Methyl-9,10-ethanoanthracene-9(10H)-propanamine); fluoxetine; histamine; 3-(2-aminoethyl)pyrazole; 2-(diphenylmethoxy)-N-methylethylamine; 2-[α-[2-methylamino)ethoxy]-α-methylbenzyl]pyridine; and 6-aminopenicillanic acid.

Additional compounds according to Formula I are made by reacting reacting 2-(4'-chlorosulfonylphenyl)-5-(4"-dimethylaminophenyl)oxazole (2, DAPOXYL sulfonyl chloride) with any one of the following amines: sulfuric acid monoaminoethyl ester; sulfuric acid mono-(3-aminopropyl) ester; sulfuric acid monoaminoethyl ester ethyl ester; sulfuric acid mono-(3-aminopropyl)ester ethyl ester; (1-aminopropyl)sulfonic acid; (1-amino-2-methylpropyl)sulfonic acid; (1-aminobutyl)sulfonic acid; (1-aminohexyl)sulfonic acid; (1-aminoethyl)sulfonic acid (1-aminoethyl)sulfonic acid diisopropyl ester; (2-benzylaminoethyl)sulfonic acid monoethyl ester; (1-aminopropyl)sulfinic acid; (1-amino-2-methylpropyl)sulfinic acid; (1-aminobutyl)sulfinic acid; (1-aminohexyl)sulfinic acid; (1-aminoethyl)sulfinic acid; (1-aminoethyl)sulfinic acid diisopropyl ester; and (2-benzylaminoethyl)sulfinic acid monoethyl ester.

Additional compounds according to Formula I are made by further modifying a compound made according to Scheme I. When, in compound 1, $R^1$ is a $NHR^3$, said $R^1$ may be converted into one of the following functional groups to produce an additional compound according to Formula I: $-NR^3C(O)R^4$, $-NR^3C(O)OR^4$, amidino, guanidino, biguanidino, alkyliminoamino, formyliminoamino, and a chelator. The transformation of $NHR^3$ into one of $-NR^3C(O)R^4$, $-NR^3C(O)OR^4$, amidino, guanidino, biguanidino, alkyliminoamino, formyliminoamino, and a chelator, is performed using chemical reactions well known in the art. For example, guanidinylation of the terminal amine is achieved using standard reagents such as aminoiminosulfonic acid (Miller, A. E. and Bischoff, J. J. Synthesis 777 (1986)), or 1H-pyrazole-1-carboxamidine hydrochloride (Bernatowicz, M. S. et. al. *J. Org. Chem.* 57:2497 (1992)), or with substituted guanidinylating reagents such as N,N'-bis(tert-butoxycarbonyl)-S-methylisothiourea (Bergeron, R. J, and McManis, J. S. J. Org. Chem. 52:1700 (1987)) or $NR^a$, $NR^b$, $N^c$-1H-pyrazole-1-carboxamidine, where $R^a$, $R^b$ and $R^c$ are defined as above for Formula I. Useful 1H-pyrazole-1-carboxamidines include N,N'-bis(tert-butoxycarbonyl)-1H-pyrazole-1-carboxamidine and N-N'-bis(benzyloxycarbonyl)-1H-pyrazole-1-carboxamidine (all of which can be prepared according to Bernatowicz, M. S. et. al, *Tetrahedron Lett.* 34:3389(1993)).

Further, when, in compound 1, $R^1$ is a OH, additional compounds according to Formula I are made by converting said OH to one of the following groups: cycloalkyl, cycloalkenyl, cycloheteroalkyl, cycloheteroalkenyl, aryl, heteroaryl, $-OR^3$, $-NR^3R^4$, $-SR^3$, $-S(O)R^3$, $-S(O)_2R^3$, $-C(O)H$, $-C(O)R^3$, $-OC(O)R^3$, $-C(O)NR^3R^4$, $-NR^3C(O)R^4$, $-OC(O)OR^3$, $-OC(O)NR^3R^4$, $-NR^3C(O)OR^4$, $-OS(O)_2OR^3$, $-S(O)_2OR^3$, $-OP(O)(OR^3)OR^4$, or $-P(O)(OR^3)OR^4$, amidino, guanidino, biguanidino, oxyguanidino, alkyliminoamino, formyliminoamino, or a chelator. For example, when, in a compound according to Formula I, $R^1$ is OH, additional compounds according to Formula I are made by reacting compound 1 with Cl—C(O)$R^3$, producing a compound according to Formula I wherein $R^1$ is —OC(O)$R^3$.

Many other chemical reactions and transformations are used to produce additional compounds according to Formula I. Said chemical reactions and transformations are used to change, for example, $R^1$ of compound 1. Alternatively, said chemical reactions and transformations are used to modify either A or $R^2$ to produce yet additional compounds according to Formula I. Said chemical reactions and transformations are well-known to one of ordinary skill in the art. For example, see March, J., "Advanced Organic Chemistry: Reactions, Mechanisms, and Structure," 4th ed., New York: Wiley, 1992; Larock, R. C., "Comprehensive Organic Transformations: A Guide to Functional Group Preparations," $2^{nd}$ Ed., New York: Wiley-VCH, 1999; and Greene, T. W., "Protective Groups in Organic Synthesis," New York: Wiley, 1981.

EXAMPLE 1

Compounds According to Formula I

The following compounds are examples of compounds according to Formula I. Compounds 9–21 are or were made according to the procedure shown in Scheme 1.

4-[5-(4-Dimethylaminophenyl)oxazol-2-yl]-N-(2-pyrrolidin-1-ylethyl)benzenesulfonamide (9)

Compound 9 was made by reacting compound 2 with 2-(1-pyrrolidinyl)ethylamine. Compound 9 has the following characteristics: molecular weight (MW): 440.566; mass spectrum (M+H): 441.4.

4-[5-(4-Dimethylaminophenyl)oxazol-2-yl]-N-[3-(4-methyl-piperazin-1-yl)propyl]benzenesulfonamide (10)

Compound 10 was made by reacting compound 2 with 3-(4-methylpiperazinyl)-1-propylamine. Compound 10 has the following characteristics: molecular weight (MW): 483.635; mass spectrum (M+H): 484.4.

Dimethyl-(4-{2-[4-(piperazine-1-sulfonyl)phenyl]oxazol-5-yl}phenyl)amine (11)

Compound 11 was made by reacting compound 2 with piperazine. Compound 11 has the following characteristics: molecular weight (MW): 412.513; mass spectrum (M+H): 413.5; mass spectrum (2M+Na): 847.1.

Dimethyl-(4-{2-[4-(4-methylpiperazine-1-sulfonyl)phenyl]-oxazol-5-yl}phenyl)amine (12)

Compound 12 was made by reacting compound 2 with 4-methylpiperazine. Compound 12 has the following characteristics: molecular weight (MW): 426.539; mass spectrum (M+H): 427.5.

4-[5-(4-Dimethylaminophenyl)oxazol-2-yl]-N-(4-methylpiperazin-1-yl)-benzenesulfonamide (13)

Compound 13 was made by reacting compound 2 with 1-amino-4-methylpiperazine. Compound 13 has the following characteristics: molecular weight (MW): 441.554; mass spectrum (M+H): 442.6.

2-{4-[5-(4-Dimethylaminophenyl)oxazol-2-yl]-benzenesulfonylamino}succinic acid (14)

Compound 14 was made by reacting compound 2 with aspartic acid. Compound 14 has the following characteristics: molecular weight (MW): 459.48; mass spectrum (M+H): 460.3.

{4-[5-(4-Dimethylaminophenyl)oxazol-2-yl]-benzenesulfonylamino}acetic acid (15)

Compound 15 was made by reacting compound 2 with glycine. Compound 15 has the following characteristics: molecular weight (MW): 401.443; mass spectrum (M+H): 402.6.

({4-[5-(4-Dimethylaminophenyl)oxazol-2-yl]benzenesulfonyl}-methylamino)acetic acid (16)

Compound 16 was made by reacting compound I with 3-aminopropanoic acid. Compound 16 has the following characteristics: molecular weight (MW): 415.47; mass spectrum (M+H): 416.3.

4-[5-(4-dimethylaminophenyl)oxazol-2-yl]-N-(2-guanidinoethyl)benzenesulfonamide (17)

Compound 17 was made by reacting 4-[5-(4-dimethylaminophenyl)oxazole-2-yl]-N-(2-aminoethyl)benzene-sulfonamide with N,N'-bis(tert-butoxycarbonyl)-1H-pyrazole-1-carboxamidine. The resulting bis-Boc protected guanidino compound was then deprotected using standard deprotection chemistry to provide compound 17. Compound 17 has the following characteristics: molecular weight (MW): 428.551; mass spectrum (M+H): 429.5.

4-[5-(4-dimethylaminophenyl)oxazol-2-yl]-N-(2-hydroxy-1,1-bis-hydroxymethylethyl)benzenesulfonamide (18)

Compound 18 was made by reacting compound 2 with tromethamine. Compound 18 has the following characteristics: molecular weight (MW): 447.512; mass spectrum (M+H): 448.4; mass spectrum: (2M+Na): 916.9.

3-{4-[5-(4-Dimethylaminophenyl)oxazol-2-yl]benzenesulfonyl}thiazolidine-2,4-dicarboxylic acid dimethyl ester (19)

Compound 19 was made by reacting compound 2 with 2,4-(dimethoxycarbonyl)thiazolidine. Compound 19 has the following characteristics: molecular weight (MW): 531.61; mass spectrum (M+H): 532.6.

2-amino-5-{4-[5-(4-dimethylaminophenyl)oxazol-2-yl]-benzenesulfonylamino}pentanoic acid (20)

Compound 20 is made by reacting compound 2 with 2,5-diaminopentanoic acid. Compound 20 has the following characteristics: molecular weight (MW): 458.532.

3-{4-[5-(4-Dimethylamino-phenyl)-oxazol-2-yl]-benzenesulfonyl}-thiazolidine-2,4-dicarboxylic acid (21)

Compound 21 is made by reacting compound 19 with LiOH to saponify the diester. Compound 21 has the following characteristics: molecular wieght (MW): 503.550.

EXAMPLE 2

Comparison of Fluorescence Emission Spectra of a Diphenyl Oxazole Derivative Dye in Different Environments 4-[5-(4-dimethylaminophenyl)oxazol-2-yl]-N-(2-guanidinoethyl)-benzenesulfonamide was mixed with different solvents to yield a final dye concentration of 10 µM. The spectra of this dye in methanol (MeOH), dimethyl sulfoxide (DMSO), and aqueous buffer (50 mM HEPES, pH7.5, 150 mM sodium chloride) are shown in FIG. 1. This figure illustrates the marked enhancement in emission intensity (200–500 fold) observed for this dye when it is shifted from an aqueous environment to a nonaqueous environment. The 4-[5-(4-dimethylaminophenyl)oxazol-2-yl]-N-(2-guanidinoethyl)benzenesulfonamide was mixed with a 0.1 mg/mL solution of thrombin, a protein, in buffer (50 mM HEPES, pH7.5, 150 mM sodium chloride), to yield a final dye concentration of 10 µM. The fluorescence emission spectra of this solution were recorded both immediately after mixing and also following heating of the solution to 80° C. for 5 minutes. The native thrombin/dye spectrum shows the fluorescence emission before heating and the unfolded thrombin/dye spectrum shows the fluorescence emission after heating. These two spectra illustrate that a substantial enhancement in fluorescence emission occurs when 4-[5-(4-dimethylaminophenyl)oxazol-2-yl]-N-(2-guanidinoethyl)-benzenesulfonamide binds to unfolded protein, and the emission from dye bound to unfolded protein has a favorably red-shifted maximum at 520 nm, compared to an emission maximum at approximately 460 nm for 5-(4"-dimethylaminophenyl)-2-(4'-phenyl)oxazole sulfonate and 1,8-anilinonaphthylene sulfonate.

EXAMPLE 3

Use of a Diphenyl Oxazole Derivative Dye to Measure an Unfolding Transition for a Protein that Fails to Produce Data With Other Dyes 4-[5-(4-dimethylaminophenyl)oxazol-2-yl]-N-(2-guanidinoethyl)-benzenesulfonamide, 5-(4"-dimethylaminophenyl)-2-(4'-phenyl)oxazole sulfonate, and 1,8-anilino-napthylene sulfonate were mixed with a protein, PPAR-gamma, each in separate wells of a polypropylene 384-well plate. Each solution consisted of 100 µM of each dye mixed with 0.2 mg/mL protein in a buffer consisting of 25 mM HEPES pH 7.9, 200 mM NaCl, 5 mM dithiothreitol, and 1 mM EDTA. Individual fluorescence curves generated by heating to different temperatures in a Thermofluor® instrument are shown in FIG. 3. This figure illustrates that certain proteins such as PPAR-γ fail to produce a measurable transition in the presence of the two sulfonate dyes, whereas the unfolding of this protein can be readily monitored by measuring the enhanced fluorescence of 4-[5-(4-dimethylaminophenyl)oxazol-2-yl]-N-(2-guanidinoethyl)-benzenesulfonamide dye upon its binding to the unfolded form of the protein.

EXAMPLE 4

Monitoring of the Endoplasmic Reticulum

Mouse pancreatic acinar cells are isolated by 6 minutes in CLSPA collagenase (Worthington, USA.) Cells are whole-cell patch clamped, and the $CaCl_2$ current is recorded under conditions as described in Kidd, et al., *J. Physiol.* 520: 187–201 (1999). Local secretory pole $Ca^{2+}$ spikes are induced by the infusion of 10 mM inositol-2,4,5-triphosphate through the patch pipette. In two separate experiments, a compound of Formula I is employed to visualize the distribution of the ER using either eide-field fluorescence microscopy or two-photon excitation microscopy (Leica TCS-SP-MP, Germany). The cells are incubated with 100–200 nM compound of Formula I for 30 minutes and viewed with excitation light of 400 nm (xenon light source, wide-field; or by a pumped titanium/sapphire laser tuned to 800 nm, two-photon). Emission light is collected at 450–700 nm. After initial visualization of the cellular organelles, additional compounds or agents are administered. In one experiment, 100 µM nocodazole is administered to the cells in addition to the compound of Formula I. In a second experiment, 10 mM TAXOL is administered to the cells in addition to the compound of Formula I.

All patents, publications, and other references cited herein are hereby fully incorporated by reference.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method of using a compound of Formula I to monitor an environment, wherein said environment is a cell, said method comprising:
   (a) placing said compound in or near said environment;
   (b) exposing said compound to a light source, wherein said light source produces light with wavelengths between 200 and 700 nm; and
   (c) detecting a fluorescent energy, wherein said fluorescent energy is emitted by said compound; wherein the compound of Formula I is:

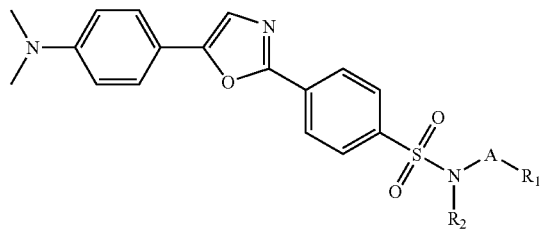

Formula I wherein

A is a single bond, alkylene, alkenylene, or alkynylene, wherein any of alkylene, alkenylene, and alkynylene is optionally substituted;

$R^1$ is cycloalkyl, cycloalkenyl, piperazine, pyrrolidine, imidazole, aryl, —$OR^3$, —$SR^3$, —$S(O)R^3$, —$S(O)_2R^3$, —C(O)H, —C(O)OR$^3$, —OC(O)R$^3$, —C(O)NR$^3$R$^4$, —NR$^3$C(O)R$^4$, —OC(O)OR$^3$, —OC(O)NR$^3$R$^4$, NR$^3$C(O)OR$^4$, —OS(O)$_2$OR$^3$, —S(O)$_2$OR$^3$, —S(O)OR$^3$, —OP(O)(OR$^3$)OR$^4$, —P(O)(OR$^3$)OR$^4$, —P(O)HOR$^3$, amidino, guanidino, biguanidino, oxyguanidino, alkyliminoamino, formyliminoamino, or EDTA; and R$^2$ is H, alkyl, alkenyl, alkynyl, aryl, arylalkyl, or cycloalkyl, wherein any of alkyl, alkenyl, alkynyl, aryl, arylalkyl, and cycloalkyl is optionally substituted; and R$^3$ and R$^4$ are independently H, alkyl, alkenyl, alkynyl, aryl, or arylalkyl, wherein any of alkyl, alkenyl, alkynyl, aryl, and arylalkyl, is optionally substituted;

or wherein

A is a single bond; and R$^1$, R$^2$, and A, together with N to which R$^1$, R$^2$, and A are attached, form a piperazine or thiazolidine, either of which is optionally substituted; and salts thereof;

with the provisos that, when A is C$_{1-8}$ unsubstituted alkyl and R$^2$ is H or methyl, then R$^1$ is not —NH$_2$, —NHCH$_3$, —N(CH$_3$)$_2$, or —NHC(O)CH$_2$Br;

when A is C$_{1-3}$ unsubstituted alkyl and R$^2$ is H, then R$^1$ is not —C(O)OH, —C(O)OCH$_3$, or —C(O)OCH$_2$CH$_3$;

when A is C$_{1-3}$ unsubstituted alkyl and R$^2$ is H, then R$^1$ is not —NHC(O)C$_6$F$_5$;

when A is a single bond and R$^2$ is H or CH$_3$, then R$^1$ is not phenyl substituted with —B(OH)$_2$; and when A is a single bond, R$^1$, R$^2$, and A, together with N to which R$^1$, R$^2$, and A are attached, do not form unsubstituted morpholinyl.

2. The method of claim 1, wherein said light source produces light with wavelengths between 300 and 600 nm.

3. The method of claim 2 performed as a fluorescence thermal shift assay.

4. The method of claim 2, wherein said environment is an endoplasmic reticulum of said cell.

5. The method of claim 2, wherein said compound is used as a hydroxy reactive probe.

6. The method of claim 2, wherein said compound is used as a amine reactive probe.

7. The method of claim 2, wherein said compound is used as a ketone reactive probe.

* * * * *